US008067670B2

(12) United States Patent
Landschuetze et al.

(10) Patent No.: US 8,067,670 B2
(45) Date of Patent: Nov. 29, 2011

(54) PLANTS THAT PRODUCE AMYLOPECTIN STARCH WITH NOVEL PROPERTIES

(75) Inventors: Volker Landschuetze, Berlin (DE); Jens Pilling, Berlin (DE); Stephan Soyka, Berlin (DE)

(73) Assignee: Bayer CropScience AG, Monheim am Rhein (DE)

( * ) Notice: Subject to any disclaimer, the term of this patent is extended or adjusted under 35 U.S.C. 154(b) by 859 days.

(21) Appl. No.: 11/630,149

(22) PCT Filed: Jun. 20, 2005

(86) PCT No.: PCT/EP2005/006862
§ 371 (c)(1),
(2), (4) Date: Jan. 31, 2008

(87) PCT Pub. No.: WO2005/123927
PCT Pub. Date: Dec. 29, 2005

(65) Prior Publication Data
US 2008/0251225 A1 Oct. 16, 2008

(30) Foreign Application Priority Data

Jun. 21, 2004 (DE) .......................... 10 2004 029 763

(51) Int. Cl.
C12N 15/82 (2006.01)
C12N 15/00 (2006.01)
C12N 15/09 (2006.01)
C12N 15/113 (2006.01)
C12N 15/29 (2006.01)
A01H 5/00 (2006.01)
A01H 5/10 (2006.01)
C07H 21/02 (2006.01)

(52) U.S. Cl. ........ 800/284; 800/285; 800/286; 800/290; 800/295; 800/278; 435/320.1; 435/468; 536/23.1; 536/23.6; 536/24.5

(58) Field of Classification Search .......................... None
See application file for complete search history.

(56) References Cited

U.S. PATENT DOCUMENTS 6,940,001 B1 * 9/2005 Landschutze ................. 800/284

FOREIGN PATENT DOCUMENTS

| EP | 0 779 363 A2 | 6/1997 |
| WO | WO 92/14827 | 9/1992 |
| WO | WO 95/26407 | 10/1995 |
| WO | WO 96/15248 | 5/1996 |
| WO | WO 00/08184 | 2/2000 |
| WO | WO 00/66745 | 11/2000 |
| WO | WO 01/12782 | 2/2001 |
| WO | WO 01/19975 | 3/2001 |

OTHER PUBLICATIONS

Hovenkamp-Mermelink et al 1987 Theor. Appl. Genet. vol. 75 217-221, provided in Applicants IDS.*

Jobling et al 2002 Nature Biotechnology 20:295-299, provided by Applicant.*
Jobling, et al., "Production of a Freeze-Thaw-Stable Potato Starch by Antisense Inhibition of Three Starch Synthase Genes", Nature Biotechnology, vol. 20, p. 295-299, Mar. 2002.
Lloyd, et al., "Simultaneous Antisense Inhibition of Two Starch-Synthase Isoforms in Potato Tubers Leads to Accumulation of Grossly Modified Amylopectin", Biochem J., vol. 338, pp. 515-521, 1999.
Morell, et al., "Barley sex6 Mutants lack Starch Synthase Iia Activity and Contain a Starch with Novel Properties", The Plant Journal, vol. 34, pp. 173-185, 2003.
Kossman, et al., "Understanding and Influencing Starch Biochemistry", Critical Reviews in Plant Sciences, vol. 19, No. 3, pp. 171-226, 2000.
Shure, et al., "Molecular Identification and Isolation of the Waxy Locus in Maize", Cell, vol. 35, pp. 225-233, Nov. 1983.
Hovenkamp-Mermelink, et al., "Isolation of an Amylose-Free Starch Mutant of the Potato (*Solanum tuberosum* L.)", Theor. Appl. Genet., vol. 75, 217-221, 1987.
Visser, et al., "Inhibition of the expression of the gene for granule-bound starch synthase in potato by antisense constructs", Mol. Gen. Genet., vol. 225, pp. 289-296, 1991.
Hergersberg, "Molekulare Analyse des *waxy* Gens aus *Solanum tuberosum* und Expression von *waxy* antisense RNA in transgenen kartoffeln", Inaugural-Dissertation, zur Erlangung des Doktorgrades der Mathematisch-Naturwissenschaftlichen Fakultät der Universität zu Köln, 1988.
Abel, et al., Cloning and Functional Analysis of a cDNA encoding a Novel 139 kDa Starch Synthase from Potato (*Soloanum tuberosum* L.), The Plant Journal, vol. 10, No. 6, p. 981-991, 1996.
Abel, Untersuchungen zur Funktion von Stärke-Synthasen in derKartoffel (*Solanum tuberosum* L.), Inaugural-Dissertation, zur Erlangung des Doktorgrades der Fachbereich Biologie der Freien Universität Berlin, 1995.
Koßmann, "Cloning and Expression Analysis of a Potato cDNA that encodes branching Enzyme: Evidence for co-expression of starch biosynthetic genes", Mol. Gen. Genet., vol. 230, pp. 39-44, 1991.
Marshall, et al., "Identification of the Major Starch Synthase in the Soluble Fraction of Potato Tubers", The Plant Cell, vol. 8, p. 1121-1135, Jul. 1996.
Safford, et al., "Consequences of antisense RNA inhibition of starch branching enzyme activity on properties of potato starch", Carbohydrate Polymers, Vo. 35, pp. 155-168, 1998.
Li, et al., "The Structure and Expression of the Wheat Starch Synthase III Gene. Motifs in the Expressed Gene Define the Lineage of the Starch Synthase III Gene Family", Plant Physiology, vol. 123, pp. 613-624, Jun. 2000.
Gao, et al., "Characterization of *dull 1*, a Maize Gene Coding for a Novel Starch Synthase", The Plant Cell, vol. 10, p. 399-412, Mar. 1998.
Smith-White, et al., "Suggested Mnemonics for Cloned DNA Corresponding to Enzymes Involved in Starch Metabolism", Plant Molecular Biology Reporte, vol. 12, No. 2, pp. S67-S71, 1994.

(Continued)

*Primary Examiner* — Brent T Page
(74) *Attorney, Agent, or Firm* — Hunton & Williams LLP

(57) ABSTRACT

The present invention relates to genetically modified plant cells and plants in which the genetic modification leads to a reduction in GBSSI, SSIII and BEI activity in comparison to the activity in corresponding wild type plant cells or wild type plants. Furthermore, the present invention relates to methods for the production of such plant cells and plants. The present invention also relates to the starch produced by the plant cells of the invention or plants of the invention, as well as to methods for the production of this starch and derivatised starch.

49 Claims, No Drawings

OTHER PUBLICATIONS

Larsson, et al., "Molecular Cloning and Characterization of Starch-Branching Enzyme II from Potato", Plant Molecular Biology, vol. 37, pp. 505-511, 1998.

Baba, et al., "Sequence Conservation of the Catalytic Regions of Amylolytic Enzymes in Maize Branching Enzyme-I", Biochemical and Biophysical Research Communications, vol. 181, No. 1, p. 87-94, Nov. 27, 1991.

Kim, et al., "Genomic Organization and Promoter Activity of the Maize Starch Branching Enzyme I Gene", Gene, vol. 216, pp. 233-243, 1998.

Hovenkamp-Hermelink, et al., "Rapid Estimation of the Amylose/amylopectin Ration in Small Amounts of Tuber and Leaf Tissue of the Potato", Potato Research, vol. 31, p. 241-246, 1988.

Nielsen, et al., "Starch Phosphorylation in Potato Tubers Proceeds Concurrently with de Novo Biosynthesis of Starch", Plant Physiol., vol. 105, p. 111-117, 1994.

Rocha-Sosa, et al., "Both Developmental and Metabolic Signals Activate the Promoter of a Class I Patatin Gene", The EMBO Journal, vol. 8, No. 1, p. 23-29, 1989.

* cited by examiner

PLANTS THAT PRODUCE AMYLOPECTIN STARCH WITH NOVEL PROPERTIES

CROSS-REFERENCE TO RELATED APPLICATIONS

This application is a U.S. national stage application of International Application No. PCT/EP2005/006862, filed on Jun. 20, 2005, which claims the benefit of German Application Serial No. DE 10 2004 029 763.0, filed on Jun. 21, 2004, the disclosures of each of which are herein incorporated by reference in their entireties.

BACKGROUND OF THE INVENTION (i) Field of the Invention

The present invention relates to genetically modified plant cells and plants in which the genetic modification leads to the synthesis of amylopectin starch with novel properties. Furthermore, the present invention relates to methods for the production of such plant cells and plants. The present invention also relates to starches produced by the plant cells and plants of the invention and methods for the production of these starches and derivatised starches.

(ii) Description of the Related Art

In view of the increasing significance that is currently being attributed to vegetable ingredients as sources of renewable raw materials, one of the objectives of bioengineering research is concerned with the adaptation of these vegetable raw materials to the requirements of the processing industry. In order to be able to utilise renewable raw materials in as many areas as possible it is additionally necessary to identify a wide variety of substances.

Starch is a complex mixture of polysaccharides that are composed of chemically unique base components, glucose molecules. However, polysaccharide molecules differ in respect of the degree of polymerisation and branching, which influences the physico-chemical properties of starch. A differentiation is made between amylose starch, i.e. starch that is comprised mainly of amylose, and amylopectin starch, i.e. starch that is comprised mainly of amylopectin.

For a considerable time amylose was regarded as a linear polymer, consisting of α-1,4-glycosidically linked α-D-glucose monomers. However, more recent studies have proven the presence of α-1,6-glycosidic branching points (approx. 0.1%) (Hizukuri and Takagi, 1984, Carbohydr. Res. 134, 1-10; Takeda et al., 1984, Carbohydr. Res. 132, 83-92).

Amylopectin consists of a complex mixture of variably branched glucose chains. Unlike amylose, amylopectin is more highly branched. Side chains are linked to the primary chain, consisting of α-1,4-glycosidically linked α-D-glucose monomers, by way of α-1,6-glycosidic bonds. According to textbook data (Voet and Voet, Biochemistry, John Wiley & Sons, 1990), the α-1,6 branches occur on average every 24 to 30 glucose moieties. This corresponds to a degree of branching of approx. 3%-4%. The data regarding the degree of branching are variable and dependent on the origin of the respective starch (e.g. plant species, plant variety, etc.). In plants that are typically used for industrial starch production such as, for example, maize, wheat or potato, the starch synthesised is comprised of approx. 20%-30% amylose starch and approx. 70%-80% amylopectin starch. Another fundamental difference between amylose and amylopectin lies in the molecular weight. amylose, depending on the origin of the starch, has a molecular weight of $5 \times 10^5$-$10^6$ Da, in the case of amylopectin it lies between $10^7$ and $10^8$ Da. The two macromolecules can be differentiated on the basis of their molecular weight and their differing physico-chemical properties, which can be seen most readily in their different iodine binding properties.

In addition to the amylose/amylopectin ratio and the phosphate content the functional characteristics of the starch are strongly influenced by the molecular weight, the side chain distribution pattern, the ion content, the lipid and protein content, the average starch granule size and the starch granule morphology. Examples of important functional characteristics are the solubility, the retrogradation behaviour, the water binding capability, the film formation properties, the viscosity, the gelatinisation properties, the freeze/thaw stability, the acid stability, the gel solidity, etc.

The gelatinisation properties, which include the end viscosity, can be determined by the person skilled in the art with various methods. Depending on the method used, absolute values in particular, but also relative values, can differ for the same starch sample. A quick and efficient method for the analysis of gelatinisation properties is the RVA analysis. Depending on the parameters selected and the temperature profile during the RVA analysis, different RVA profiles are obtained for the same sample. It should be noted that in the following quoted documents, which explain the state of the art, different profiles are sometimes described for determining the agglutination properties.

It is known that plants can be genetically modified in such a way that they produce starch that can be differentiated on the basis of physico-chemical parameters from the starch that is manufactured by corresponding plants that have not been genetically modified. A review of various plant species that exhibit a reduction in enzymes involved in the starch biosynthesis has been described by Kossmann and Lloyd (2000, Critical Reviews in Plant Sciences 19(3), 171-126).

In conjunction with the present invention the following state of the art is of interest. Plants have hitherto been described in which the activity of the starch granule-bound starch synthase GBSSI ("Granule-Bound Starch Synthase") is reduced (Shure et al., 1983, Cell 35, 225-233; Hovenkamp-Hermelink et al., 1987, Theoretical and Applied Genetics 75, 217-221; Visser et al., 1991, Mol. Gen. Genet. 225, 289-296; Hergersberg, 1988, Dissertation, Universität Köln; WO 92/11376). The GBBSI is involved in the formation of amylose. Inhibition of the GBSSI activity leads to a synthesis of starch that is comprised almost exclusively of amylopectin. The corresponding GBSSI gene in the maize plant is known by the term "waxy".

Furthermore, plants have been described in which the activity of soluble starch synthase SSIII is reduced (Abel et al., 1996, The Plant Journal 10(6), 981-991; Lloyd et al., 1999, Biochemical Journal 338, 515-521; WO 00/08184; WO 96/15248; EP-A 0779363). In comparison with starch isolated from corresponding wild type plants, starch from such plants exhibits a relative shift of the side chains of amylopectin from longer chains to shorter chains (Lloyd et al., 1999, Biochemical Journal 338, 515-521), an increased phosphate content, no change in the amylose content (Abel et al., 1996, The Plant Journal 10(6), 9891-9991) and a reduced end viscosity in the RVA analysis (Abel, 1995, Dissertation, Freie Universität Berlin).

Furthermore, plants have been described, in with the activity of the branching enzyme BEI is reduced (Kossmann et al., 1991, Mol. Gen. Genet. 230, 39-44; Safford et al., 1998, Carbohydrate Polymers 35, 155-168; WO 92/14827; WO 95/26407). Safford et al. (1998, supra) describe that corresponding potato plants produce a starch with an amylose/amylopectin ratio that is essentially unchanged. Nor does the degree of branching of the amylopectin differ significantly from that of starch isolated from wild type potato plants. The starch-bound phosphate content is comparably increased, however, which presumably leads to the various gelatinisation properties observed and the altered viscosity of the starch isolated from corresponding mutants as compared to starch isolated from wild type potato plants.

Plants are described in WO 01/19975, in which both the GBSSI and the SSII and/or SSIII activity are reduced. Starch from potato plants with reduced GBSSI, SSII and SSIII activity exhibits a lower amylose content, changed swelling properties and gelatinisation properties, and an increased freeze/thaw stability in comparison to starch from wild type potato plants.

Plants are described in WO 01/12782, in which both the GBSSI and the BEI activity are reduced. In comparison to starch from wild type plants, starch from these plants exhibits a reduced amylose content, and in comparison to starch from plants of the waxy phenotype an increased phosphate content and/or lowered gelatinisation temperature. Plants are described in WO 00/08184, in which both the SSIII and the BEI activity are reduced. In comparison to starch from wild type plants starch from such plants exhibits an increased phosphate content.

SUMMARY OF THE INVENTION

The object of the present invention is to provide amylopectin starches with new properties, new plant cells and/or plants that produce such starches, as well as means and methods for the generation of said plant cells and/or plants.

Subject of the present invention is genetically modified plant cells and plants in which the genetic modification leads to a reduction in the GBSSI, SSIII and BEI activity relative to the activity in corresponding wild type plant cells or wild type plants.

DETAILED DESCRIPTION OF THE INVENTION

In conjunction with the present invention, the term "GBSSI" is to be understood to mean any enzyme that belongs to the class of starch granule-bound starch synthases of the isoform I (EC 2.4.1.21).

In conjunction with the present invention, the term "GBSSI gene" is to be understood to mean a nucleic acid molecule or polynucleotide (cDNA, DNA) that codes for GBSSI. Polynucleotides coding for GBSSI are described for various plant species such as, for example, for maize (Genbank Acc. Nos. AF079260, AF079261), wheat (Genbank Acc. Nos. AB019622, AB019623, AB019624), rice (Genbank Acc. Nos. AF092443, AF092444, AF031162), barley (Genbank Acc. Nos. X07931, X07932) and potato (Genbank Acc. No. X58453). GBSSI gene preferably means a nucleic acid molecule or polynucleotide (cDNA, DNA) that codes for GBSSI from potato plants.

In conjunction with the present invention, the term "SSIII" is to be understood to mean a class of soluble starch synthases (ADP-glucose 1,4-α-D-glucan 4-α-D-glucosyltransferase; EC 2.4.1.21). Soluble starch synthases catalyse a glycosylation reaction in which glucose moieties of the ADP-glucose substrate are transferred to α-1,4-linked glucan chains with formation of a α-1,4-link (ADP-glucose+{(1,4)-α-D-glucosyl}{N}⇔ADP+{(1,4)-α-D-glucosyl}(N+1)).

For example, SSIIIs are described by Marshall et al. (1996, The Plant Cell 8, 1121-1135), Li et al. (2000, Plant Physiology 123, 613-624), Abel et al. (1996, The Plant Journal 10(6), 981-991) and in WO 00/66745. SSIIIs frequently exhibit a sequence of domains with respect to their construction and possess a signal peptide on the N-terminus for the transport of plastids. In the direction of the C-terminus there is an N-terminal region, an SSIII-specific region and a catalytic domain (Li et al., 2000, Plant Physiology 123, 613-624).

In conjunction with the present invention, the term "SSIII gene" is to be understood to mean a nucleic acid molecule or polynucleotide (DNA, cDNA) that codes for SSIII. Polynucleotides coding for SSIII are described for various plant species such as, for example, potato (Abel et al., 1996, The Plant Journal 10(6), 981-991), wheat (WO 00/66745; Li et al., 2000, Plant Physiology 123, 613-624; Genbank Acc. No. AF258608; Genbank Acc. No. AF258609), maize (Gao et al., 1998, Plant Cell 10 (3), 399-412; Genbank Acc. No. AF023159), vignia (Genbank Acc. No. AJ225088), rice (Genbank Acc. No. AY100469; Genbank Acc. No. AF43291) and *arabidopsis* (Genbank Acc. No. AC007296). SSIII gene preferably means a nucleic acid molecule or polynucleotide (cDNA, DNA) that codes for SSIII from potato plants.

In conjunction with the present invention, the term "BEI" is to be understood to mean a branching enzyme ("Branching Enzyme"=BE) of isoform I (α-1,4-glucan: α-1,4-glucan 6-glycosyltransferase; E.C. 2.4.1.18) that catalyses a transglycosylation reaction in which α-1,4 linkages of an α-1,4 glucan donor are hydrolysed, and the α-1,4 glucan chains released are transferred to an α-1,4 glucan acceptor chain and thereby converted into α-1,6 linkages. BEI preferably originates from potato plants.

The classification of the isoforms is based on the nomenclature suggested by Smith-White and Preiss (Smith-White and Preiss, 1994, Plant Mol. Biol. Rep. 12, 67-71; Larsson et al., 1998, Plant Mol. Biol. 37, 505-511). This nomenclature assumes that all enzymes that exhibit a higher homology (identity) on the amino acid level to BEI from maize (Genbank Acc. No. D11081; Baba et al., 1991, Biochem. Biophys. Res. Commun. 181 (1), 87-94; Kim et al., 1998, Gene 216, 233-243) than to BEII from maize (Genbank Acc. Nos. AF072725, U65948) are classified as "branching enzymes" of isoform I or BEI for short.

In conjunction with the present invention, the term "BEI gene" is to be understood to mean a nucleic acid molecule or polynucleotide (cDNA, DNA) that codes for BEI. Polynucleotides coding for BEI are described for various plant species such as, for example, for maize (Genbank Acc. Nos. D11081, AF072724), rice (Genbank Acc. No. D11082), peas (Genbank Acc. No. X80010) and potato. Various forms of the BEI gene or the BEI from potato plants were described, for example, by Khoshnoodi et al. (1996, Eur. J. Biochem. 242 (1), 148-155, Genbank Acc. No. Y08786) and Kossmann et al. (1991, Mol. Gen. Genet. 230, 39-44). BEI gene preferably means a nucleic acid molecule or polynucleotide (cDNA, DNA) that codes for BEI from potato plants. In potato plants the BEI gene is expressed mainly in the tubers and is almost not expressed in the leaves (Larsson et al., 1998, Plant Mol. Biol. 37, 505-511).

Within the context of the definitions of the terms "GBSSI gene", "SSIII gene" and "BEI gene" reference is made to specific polynucleotide sequences that code for the corresponding enzymes by the statement of "Genbank Acc." numbers and literary sources. In the following sections, embodiments of the present invention are described wherein polynucleotides with the specified sequences given here can be used. Of course, the invention is not restricted to the use of such precisely described sequences or parts thereof. For example, polynucleotides can also be utilised that have an identity with the specified sequences of at least 80%, preferably at least 90%, more preferably at least 95% and most preferably at least 98%.

In conjunction with the present invention, the term "identity" is to be understood to mean the number of amino acids/nucleotides in common with other proteins/nucleic acids, expressed as a percentage. The identity is preferably calculated with the aid of computer programs. If sequences that are compared with one another have differing lengths, the identity is to be calculated such that the number of amino acids which the shorter sequence has in common with the longer sequence determines the identity percentage. The identity is preferably calculated by using the well-known and publicly available computer program ClustalW (Thompson et al., 1994, Nucleic Acids Research 22, 4673-4680). ClustalW is provided for public use by Julie Thompson and Tony Gibson, European Molecular Biology Laboratory, Meyerhofstrasse 1, 69117 Heidelberg, Germany. ClustalW can also be downloaded from various internet sites, including from IGBMC (Institut de Genetique et de Biologic Moleculaire et Cellulaire, B.P.163, 67404 Illkirch Cedex, France and from EBI on the world wide web at ebi.ac.uk/pub/software/) as well as from EBI's mirrored internet: sites (European Bioinformatics Institute, Wellcome Trust Genome Campus, Hinxton, Cambridge CB10 ISD, UK).

Version 1.8 of the ClustalW computer program is preferably used to determine the identity between the proteins described herein and other proteins. The following parameters should be set: KTUPLE=1, TOPDIAG=5, WINDOW=5, PAIRGAP=3, GAPOPEN=10, GAPEXTEND=0.05, GAPDIST=8, MAXDIV=40, MATRIX=GONNET, ENDGAPS(OFF), NOPGAP, NOHGAP.

Version 1.8 of the ClustalW computer program is preferably used to determine the identity between the nucleotide sequences of the nucleic acid molecules described herein and the nucleotide sequence of other nucleic acid molecules. The following parameters should be set: KTUPLE=2, TOPDIAGS=4, PAIRGAP=5, DNAMATRIX:IUB, GAPOPEN=10, GAPEXT=5, MAXDIV=40, TRANSITIONS: unweighted.

One possibility of finding similar sequences is to perform sequence database searches. In doing this, one or more sequences are entered as a query. This query sequence is then compared with sequences that are contained in the selected databases using statistical computer programs. Such database searches (blast searches) are known to the person skilled in the art and can be performed by various providers. For example, if such a database search is performed at NCBI (National Center for Biotechnology Information, on the world wide web at ncbi.nlm.nih.gov/), the standard parameters that are indicated for the corresponding comparative search, should be used. For protein sequence comparisons (blastp), these are the following settings: Limit entrez=not activated; Filter=low complexity activated; Expect value=10; word size=3; Matrix=BLOSUM62; Gap costs: Existence=11, Extension=1. As the result of such a search, the identity percentage between the query sequence and the similar sequences found in the databases is shown, together with other parameters.

In conjunction with the present invention, the term "wild type plant cell" means plant cells that served as starting material for the production of the plant cells of the invention, i.e. their genetic information, apart from the introduced genetic modification, corresponds to the genetic information of a plant cell of the invention.

In conjunction with the present invention, the term "wild type plant" means plants that served as starting material for the production of plants of the invention, i.e. their genetic information, apart from the introduced genetic modification, corresponds to the genetic information of a plant of the invention.

In conjunction with the present invention, the term "corresponds" means that when comparing several objects, the objects that are compared with one another were kept under the same conditions. In conjunction with the present invention, the term "corresponds" in respect of wild type plant cells or wild type plants means that the plant cells or plants that are compared with one another were grown under the same culture conditions, and that they are of the same (culture) age.

In one embodiment of the present invention, the genetic modification of the plant cells of the invention or the plants of the invention is produced by mutagenesis of one or more genes. The type of mutation is irrelevant, as long as it leads to a reduction in the GBSSI and/or SSIII and/or BEI activity.

In conjunction with the present invention, the term "mutagenesis" is to be understood to mean all type of introduced mutations such as, for example, deletions, point mutations (nucleotide exchanges), insertions, inversions, gene conversions or chromosome translocations.

A mutation that leads to a reduction in the GBSSI and/or SSIII and/or BEI activity can occur spontaneously in a plant, and the corresponding plants can be selected and propagated using the methods described below.

A mutation that leads to a reduction in the GBSSI and/or SSIII and/or BEI activity can also be produced by the use of chemical agents or high-energy radiation (e.g. X-ray radiation, neutron radiation, gamma radiation, UV radiation).

Agents that can be used for the generation of chemically induced mutations and the mutations occurring as an effect of the corresponding mutagens are described, for example, by Ehrenberg and Husain (1981, Mutation Research 86, 1-113) and Miller (1972, Biologisches Zentralblatt 91 (1), 31-48). The generation of rice mutants with the use of gamma radiation, ethylmethane sulphonate (EMS), N-methyl-N-nitrosourea or sodium azide ($NaN_3$) is described, for example, by Jauhar and Siddiq (1999, Indian Journal of Genetics, 59 (1), 23-28), Rao (1977, Cytologica 42, 443-450), Gupta and Sharma (1990, Oryza 27, 217-219) and Satoh and Omura (1981, Japanese Journal of Breeding 31 (3), 316-326). The generation of wheat mutants with the use of $NaN_3$ or maleic hydrazide is described by Arora et al. (1992, Annals of Biology 8 (1), 65-69). A review of the generation of wheat mutants with the use of various types of high-energy radiation and chemical agents has been published by Scarascia-Mugnozza et al. (1993, Mutation Breeding Review 10, 1-28). Svec et al. (1998, Cereal Research Communications 26 (4), 391-396) describe the use of N-ethyl-N-nitrosourea for the generation of mutants in triticale. The use of MMS (methylmethane sulphonic acid) and gamma radiation for the generation of sorghum mutants is described by Shashidhara et al. (1990, Journal of Maharashtra Agricultural Universities 15 (1), 20-23).

The production of mutants in plant species that mainly propagate vegetatively have been described for potatoes that produce an altered starch (Hovenkamp-Hermelink et al., 1987, supra) and for mint with an increased oil yield or an altered oil quality (Dwivedi et al., 2000, Journal of Medicinal and Aromatic Plant Sciences 22, 460-463).

All these methods are fundamentally suitable for the production of plant cells of the invention or the plants of the invention.

The identification of mutations in the corresponding genes, particularly in genes that code GBSSI, SSIII or BEI, can be carried out with the aid of methods known to the person skilled in the art. In particular, analyses based on hybridisation with probes ("Southern Blot"), amplification by polymerase chain reaction (PCR), sequencing of relevant genomic nucleic acid fragments and searching for individual nucleotide exchanges can be used for this purpose. A method of identifying mutations on the basis of hybridisation patterns is, for example, searching for differences in the length of restriction fragments ("Restriction Fragment Length Polymorphism", RFLP) (Nam et al., 1989, The Plant Cell 1, 699-705; Leister and Dean, 1993, The Plant Journal 4 (4), 745-750). A method based on PCR is, for example, the analysis of differences in lengths of amplified fragments ("Amplified Fragment Length Polymorphism", AFLP) (Castiglioni et al., 1998, Genetics 149, 2039-2056; Meksem et al., 2001, Molecular Genetics and Genomics 265, 207-214; Meyer et al., 1998, Molecular and General Genetics 259, 150-160). Amplified fragments cleaved with restriction endonucleases ("Cleaved Amplified Polymorphic Sequences", CAPS) can also be used to identify mutations (Konieczny and Ausubel, 1993, The Plant Journal 4, 403-410; Jarvis et al., 1994, Plant Mol. Biol. 24, 685-687; Bachem et al., 1996, The Plant Journal 9 (5), 745-753). Methods have been described for the identification of SNP's by Qi et al. (2001, Nucleic Acids Research 29 (22), e116), Drenkard et al. (2000, Plant Physiology 124, 1483-1492) and Cho et al. (1999, Nature Genetics 23, 203-207), among others. Methods that allow many plants to be examined for mutations in specific genes within a short period of time are particularly suitable. One such method, the so-called TILLING ("Targeted Induced Local Lesions In Genomes"), is described by McCallum et al. (2000, Plant Physiology 123, 439-442).

All of these methods are fundamentally suitable for the identification of plant cells of the invention or plants of the invention.

Hoogkamp et al. (2000, Potato Research 43, 179-189) have produced stable monoploid mutants starting with a potato mutant (amf) produced by chemical mutagenesis. These plants no longer synthesise active GBSSI and therefore produce an amylose-free starch. The monoploid potato plants obtained can be used as starting material for additional mutagenesis.

A reduction in the GBSSI and/or SSIII and/or BEI activity can be achieved through a reduction in the expression of one or more genes coding for GBSSI and SSIII and BEI, respectively, and/or through a reduction in the quantity of related enzyme material in the plant cells, and/or through a reduction in the enzymatic activity of the related proteins in the plant cells.

The reduction in expression can be determined, for example, by measuring the quantity of transcripts that code for the related enzymes, e.g. with Northern Blot analysis or RT-PCR. A reduction thereby preferably means a reduction in the quantity of transcripts in comparison to that in corresponding wild type plant cells of at least 50%, preferably at least 70%, more preferably at least 85%, and most preferably at least 95%.

The reduction in the quantity of GBSSI and/or SSIII and/or BEI, which has the consequence of reducing the corresponding enzymatic activity in the plant cells, can be determined with immunological methods such as, for example, Western Blot analysis, ELISA ("Enzyme Linked Immuno Sorbent Assay") or RIA ("Radio Immune Assay"). A reduction thereby preferably means a reduction in the quantity of related protein in comparison to that in corresponding wild type plant cells of at least 50%, preferably at least 70%, more preferably at least 85%, and most preferably at least 95%.

In a further embodiment of the present invention the genetic modification of the plant cell of the invention consists of the introduction of one or more foreign nucleic acid molecules/polynucleotides, the presence and/or suppression of which leads to a reduction in the GBSSI and/or SSIII and/or BEI activity compared to that in corresponding wild type plant cells. In particular, the term genetic modification is to be understood to mean the insertion of homologous and/or heterologous and/or mutagenised foreign nucleic acid molecules/polynucleotides into a plant cell, whereby the insertion of this molecule leads to a reduction in the GBSSI and/or SSIII and/or BEI activity. Transgenic plant cells are generated in this manner.

In this context, the term "transgenic" means that the plant cells of the invention deviate with regard to their genetic information from corresponding wild type plant cells as a result of the introduction of a foreign nucleic acid molecule/polynucleotide or several foreign nucleic acid molecules/polynucleotides into the cell.

In conjunction with the present invention, the term "foreign nucleic acid molecule/polynucleotide" and "foreign nucleic acid molecules/polynucleotides" is to be understood to mean a molecule or molecules that either do(es) not occur naturally in corresponding wild type plant cells, or that do(es) not occur naturally in corresponding wild type plant cells in that particular alignment or that is located at a site in the genome of the plant cell in which it does not occur naturally. The foreign nucleic acid molecule/polynucleotide is preferably a recombinant molecule that consists of various elements, the combination or specific alignment of which does not naturally occur in plant cells.

The foreign nucleic acid molecule(s)/polynucleotide(s) used for the genetic modification can be a combined or several separate nucleic acid constructs, in particular so-called single constructs, double constructs, and triple constructs. The foreign nucleic acid molecule/polynucleotide can be, for example, a so-called "triple construct", which is understood to be a single vector for plant transformation which contains both the genetic information for inhibition of the expression of one or more endogenous GBSSI genes and the genetic information for inhibition of the expression of one or more SSIII genes and the genetic information for inhibition of the expression of one or more BEI genes, or the presence or expression of which leads to a reduction in the GBSSI, SSIII and BEI activity.

In a further embodiment, the foreign nucleic acid molecule/polynucleotide can be a so-called "double construct", which is understood to be a vector for plant transformation, which contains the genetic information for the inhibition of the expression of two or the three target genes (GBSSI, SSIII, BEI gene(s)), or the presence or expression of which leads to a reduction in the activity of two of the three enzymes (GBSSI, SSIII, BEI). The inhibition of the expression of the third target gene and/or the reduction in the activity of the third enzyme occurs in this embodiment of the invention with the aid of a separate foreign nucleic acid molecule/polynucleotide that contains the corresponding genetic information for inhibition of this third target gene.

In a further embodiment of the invention, a triple construct is not introduced into the genome of the plant cell, rather several different foreign nucleic acid molecules/polynucleotides are inserted, in which one of these foreign nucleic acid molecules is, for example a DNA molecule that represents, for example, a cosuppression construct that causes a reduction in the expression of one or more endogenous GBSSI genes, and an additional foreign nucleic acid molecule is a DNA molecule, which codes for an antisense RNA, for example, that causes a reduction in the expression of one or more endogenous SSIII and/or BEI genes. Basically, however, in the construction of the nucleic acid molecules it is suitable to use any combination of antisense, cosuppression, ribozyme and double-stranded RNA constructs or in vivo mutagenesis that leads to a simultaneous reduction in the expression of endogenous genes that code for GBSSI, SSIII and BEI, or which lead to a simultaneous reduction in GBSSI, SSIII and BEI activities.

The foreign nucleic acid molecules can be introduced into the genome of the plant cell simultaneously ("cotransformation") or sequentially, i.e. one after the other ("supertransformation").

The foreign nucleic acid molecules/polynucleotides can also be introduced into various individual plants of a species. In this way, plants can be generated, in which the activity of one enzyme (GBSSI or SSIII or BEI) or two enzymes (GBSSI and SSIII or GBSSI and BEI or SSIII and BEI) is reduced. By subsequently interbreeding plants can be produced in which the activities of all three enzymes (GBSSI, SSIII, BEI) are reduced.

Furthermore, a mutant that is characterised in that it already exhibits reduced activity of one or more enzymes (GBSSI, SSIII, BEI) can be used for the introduction of a foreign nucleic acid molecule/polynucleotide or for the production of the plant cells of the invention or plants of the invention, instead of a wild type plant cell or plant. The mutants can either be spontaneously occurring mutants or mutants that were produced with the selective use of mutagens. Methods for the production of such mutants were described above.

The plant cells of the invention can be produced by the use of so-called insertion mutagenesis (review article: Thorneycroft et al., 2001, Journal of Experimental Botany 52 (361), 1593-1601). "Insertion mutagenesis" is to be particularly understood as the insertion of transposons or so-called transfer DNA (T-DNA) into a gene coding for GBSSI and/or SSIII and/or BEI, whereby the activity of the said enzymes is thus reduced in the respective cell.

The transposons can either be such that occur naturally in a wild type plant cell (endogenous transposons), or such that do not occur naturally in the said cell, but which were rather introduced into the cell using genetic engineering methods (heterologous transposons) such as, for example, transformation of the cell. Changing the expression of genes by way of transposons is known to the person skilled in the art. A review of the use of endogenous and heterologous transposons as tools in plant biotechnology is provided by Ramachandran and Sundaresan (2001, Plant Physiology and Biochemistry 39, 234-252). The possibility of identifying mutants in which specific genes were deactivated using transposon insertion mutagenesis is described in a review by Maes et al. (1999, Trends in Plant Science 4 (3), 90-96). The production of rice mutants with the aid of endogenous transposons is described by Hirochika (2001, Current Opinion in Plant Biology 4, 118-122). The identification of maize genes with the aid of endogenous retrotransposons is described, for example, by Hanley et al. (2000, The Plant Journal 22 (4), 557-566). The possibility of producing mutants with the aid of retrotransposons and methods for identifying mutants are described by Kumar and Hirochka (2001, Trends in Plant Science 6 (3), 127-134). The activity of heterologous transposons in various species has been described for both dicotyledonous and monocotyledonous plants: e.g. for rice (Greco et al., 2001, Plant Physiology 125, 1175-1177; Liu et al., 1999, Molecular and General Genetics 262, 413-420; Hiroyuki et al., 1999, The Plant Journal 19 (5), 605-613; Jeon and Gynheung, 2001, Plant Science 161, 211-219), barley (Koprek et al., 2000, The Plant Journal 24 (2), 253-263), *Arabidopsis thaliana* (Aarts et al., 1993, Nature 363, 715-717; Schmidt and Willmitzer, 1989, Molecular and General Genetics 220, 17-24; Altmann et al., 1992, Theoretical and Applied Genetics 84, 371-383; Tissier et al., 1999, The Plant Cell 11, 1841-1852), tomato (Belzile and Yoder, 1992, The Plant Journal 2 (2), 173-179) and potato (Frey et al., 1989, Molecular and General Genetics 217, 172-177; Knapp et al., 1988, Molecular and General Genetics 213, 285-290).

Fundamentally the plant cells of the invention and the plants of the invention can be produced with the aid of both heterologous and homologous transposons, whereby in the use of homologous transposons, these are also understood to include those that occur naturally in the plant genome.

The T-DNA insertion mutagenesis is based on the fact that certain sections (T-DNA) of Ti-plasmids from *Agrobacterium* can be integrated into the genome of plant cells. The site of integration into the plant chromosome is not determined; rather it can be integrated in any arbitrary location. If the T-DNA is integrated into a section of the chromosome that represents a gene function, it can lead to a change in the gene expression and thus to a change in the activity of the protein coded by the corresponding gene. In particular, the integration of a T-DNA into the coding region of a gene frequently leads to the condition that the corresponding protein of the cell concerned can no longer be synthesised or it cannot be synthesised in an active form. The use of T-DNA insertions for the production of mutants is described, for example, for *Arabidopsis thaliana* (Krysan et al., 1999, The Plant Cell 11, 2283-2290; Atipiroz-Leehan and Feldmann, 1997, Trends in Genetics 13 (4), 152-156; Parinov and Sundaresan, 2000, Current Opinion in Biotechnology 11, 157-161) and rice (Jeon and An, 2001, Plant Science 161, 211-219; Jeon et al., 2000, The Plant Journal 22 (6), 561-570). Methods for the identification of mutants that were produced with the aid of T-DNA insertion mutagenesis are described by Young et al. (2001, Plant Physiology 125, 513-518), Parinov et al. (1999, The Plant Cell 11, 2263-2270), Thorneycroft et al. (2001, Journal of Experimental Botany 52, 1593-1601) and McKinney et al. (1995, The Plant Journal 8 (4), 613-622).

The T-DNA mutagenesis is fundamentally suitable for the production of plant cells of the invention and plants of the invention.

In a further embodiment of the present invention, the presence and/or expression of one or more foreign nucleic acid molecules/polynucleotides leads to the inhibition of the expression of endogenous genes that code for GBSSI and/or SSIII and/or BEI.

This can be achieved with various methods known to the person skilled in the art. For example, these include the expression of a corresponding antisense RNA, or a double-stranded RNA construct, the preparation of molecules or vectors that cause a cosuppression effect, the expression of a correspondingly constructed ribozyme that cleaves specific transcripts that code for GBSSI or SSIII or BEI, or the so-called "in-vivo mutagenesis". Furthermore, the reduction of GBSSI and/or SSIII and/or BEI activity (activities) can also be effected with the simultaneous expression of sense and antisense RNA molecules of the respective target gene to be repressed, preferably of the GBSSI and/or SSIII and/or BEI gene. These methods are familiar to the person skilled in the art.

In addition, it is known that the formation of double-stranded RNA molecules of promoter sequences in planta can lead to a methylation and a transcriptional deactivation of homologous copies of these promoters in trans (Mette et al., 2000, EMBO J. 19, 5194-5201).

For example, a DNA molecule that contains the entire coding sequence for GBSSI and/or SSII and/or BEI, including any flanking sequences that may be present, can be used for the inhibition of gene expression using antisense or cosuppression technology, as can DNA molecules that contain only parts of the coding sequence, although these parts must be long enough to bring about an antisense effect or cosuppression effect in the cells. In general, sequences are suitable if they have a minimum length of 15 bp, preferably they have a length of 20-30 bp, more preferably they have a length of 100-500 bp, and for very efficient antisense or cosuppression inhibition the sequences have in particular a length of over 500 bp.

The use of polynucleotide sequences that have a high degree of identity with the endogenous coding sequences for GBSSI or SSIII or BEI occurring in the plant cell, is also suitable for antisense or cosuppression approaches. The minimum identity should be greater than approx. 65%. The use of sequences with identities of at least 90%, particularly between 95 and 100%, is preferred.

Furthermore, the use of introns, i.e. non-coding regions of genes that code for GBSSI or SSIII or BEI, is also feasible for achieving an antisense or cosuppression effect.

The use of intron sequences for inhibiting the expression of genes that code for starch biosynthesis proteins has been described in WO 97/04112, WO 97/04113, WO 98/37213, WO 98/37214.

The method of achieving an antisense or cosuppression effect is known to the person skilled in the art. The method of cosuppression inhibition has been described, for example, by Jorgensen (1990, Trends Biotechnol. 8, 340-344), Niebel et al. (1995, Top. Microbiol. Immunol. 197, 91-103), Flavell et al. (1995, Curr. Top. Microbiol. Immunol. 197, 43-46), Palaqui and Vaucheret (1995, Plant Mol. Biol. 29, 149-159), Vaucheret et al. (1995, Mol. Gen. Genet. 248, 311-317), de Borne et al. (1994, Mol. Gen. Genet. 243, 613-621).

The expression of ribozymes for the reduction of activity of certain enzymes in cells is also known to the person skilled in the art and is described, for example, in EP-BI 0321201. The expression of ribozymes in plant cells has been described, for example, by Feyter et al. (1996, Mol. Gen. Genet. 250, 329-338).

Furthermore, the reduction in the GBSSI and/or SSIII and/or BEI activity in the plant cells can also be achieved with so-called "in vivo mutagenesis", in which a hybrid RNA-DNA oligonucleotide ("chimeroplast") is introduced into cells through transformation of cells (Kipp et al., Poster Session at the 5$^{th}$ International Congress of Plant Molecular Biology, 21-27 Sep. 1997, Singapore; R. A. Dixon and C. J. Arntzen, Meeting Report on Metabolic Engineering in Transgenic Plants, Keystone Symposia, Copper Mountain, Colo., USA, 1997, TIBTECH 15, 441-447; WO 95/15972; Kren et al., 1997, Hepatology 25, 1462-1468; Cole-Strauss et al., 1996, Science 273, 1386-1389; Beetham et al., 1999, PNAS 96, 8774-8778).

One part of the DNA component of the RNA-DNA oligonucleotide is homologous with a polynucleotide sequence of an endogenous GBSSI and/or SSIII and/or BEI gene, but unlike the polynucleotide sequence of an endogenous GBSSI or SSIII or BEI gene it exhibits a mutation or contains a heterologous region that is surrounded by the homologous regions. The mutation or heterologous region contained in the DNA component of the RNA-DNA oligonucleotide can be transferred into the genome of a plant cell through base pairing of the homologous regions of the RNA-DNA oligonucleotide and the endogenous polynucleotide, followed by homologous recombination. This leads to a reduction in the activity of GBSSI and/or SSIII and/or BEI.

Furthermore, the reduction in the GBSSI and/or SSIII and/or BEI activity (activities) in the plant cells can also be effected through the simultaneous expression of sense and antisense RNA molecules of the respective target gene to be repressed, preferably of the GBSSI and/or SSIII and/or BEI gene.

This can be achieved, for example, through the use of chimeric constructs that contain "inverted repeats" of the respective target gene or parts of the target gene. The chimeric constructs thus code for sense and antisense RNA molecules of the respective target gene. Sense and antisense RNA are synthesised simultaneously as an RNA molecule in planta, whereby sense and antisense RNA are separated from one another by a spacer and can form a double-stranded RNA molecule (RNAi technology).

It has been shown that the introduction of inverted repeat DNA constructs into the genome of plants is a very efficient method for repressing the genes corresponding to the inverted repeat DNA constructs (Waterhouse et al., 1998, Proc. Natl. Acad. Sci. USA 95, 13959-13964; Wang and Waterhouse, 2000, Plant Mol. Biol. 43, 67-82; Singh et al., 2000, Biochemical Society Transactions 28 (6), 925-927; Liu et al., 2000, Biochemical Society Transactions 28 (6), 927-929; Smith et al., 2000, Nature 407, 319-320; WO 99/53050). Sense and antisense sequences of the target gene or target genes can also be expressed separately from one another using identical or different promoters (Nap et al., 6$^{th}$ International Congress of Plant Molecular Biology, 18-24 Jun. 2000, Quebec, Poster S7-27, Lecture Session S7).

The reduction in the GBSSI and/or SSIII and/or BEI activity (activities) in the plant cells can thus also be achieved through the production of double-stranded RNA molecules of GBSSI or SSIII or BEI genes. Preferably, "inverted repeats" of DNA molecules that are derived from GBSSI or SSIII or BEI genes or cDNAs, are introduced into the genome of plants in which the DNA molecules to be transcribed (GBSSI or SSIII or BEI gene or cDNAs or fragments of these genes or cDNAs) are under the control of a promoter that regulates the expression of the abovementioned DNA molecules.

Furthermore, it is known that the formation of double-stranded RNA molecules of promoter DNA molecules in plants in trans can lead to a methylation and a transcriptional inactivation of homologous copies of these promoters, which is hereinafter designated as target promoters (Mette et al., 2000, EMBO J. 19, 5194-5201).

Therefore, it is possible to reduce the gene expression of a particular target gene (GBSSI, SSIII, BEI gene) that is naturally under the control of a target promoter by deactivation of this target promoter.

This means that DNA molecules that contain the target promoters of the genes to be repressed (target genes) are not used as control elements for the expression of genes or cDNA in this case, but they are rather used themselves as transcribable DNA molecules, which is in contrast to the original function of promoters in plants.

For the production of the double-stranded target promoter RNA molecules in planta, which can occur there as RNA hairpin molecules, constructs are preferably used that contain "inverted repeats" of the target promoter DNA molecules whereby the target promoter DNA molecules are under the control of a promoter that regulates the gene expression of the said target promoter DNA molecules. These constructs are subsequently introduced into the genome of plants. The expression of the "inverted repeats" of the said target promoter DNA molecules leads to the formation of double-stranded target promoter RNA molecules in planta (Mette et al., 2000, EMBO J. 19, 5194-5201). The target promoter can be inactivated in this manner.

Therefore, the reduction in the GBSSI and/or SSIII and/or BEI activity in the plant cells can also be achieved through the production of double-stranded RNA molecules of promoter sequences of GBSSI or SSIII or BEI genes. Preferably, "inverted repeats" of promoter DNA molecules of GBSSI and/or SSIII and/or BEI promoters are introduced into the genome of plants whereby the target promoter DNA molecules (GBSSI, SSIII, BEI promoters) to be transcribed are under the control of a promoter that regulates the expression of the said target promoter DNA molecules.

Furthermore, it is known to the person skilled in the art that a reduction in the GBSSI and/or SSIII and/or BEI activity (activities) can be achieved through the expression of non-functional derivatives, particularly trans-dominant mutants, of the enzymes and/or through the expression of antagonists/inhibitors of the enzymes.

Antagonists/inhibitors of the enzymes can be, for example antibodies, antibody fragments or molecules with similar bonding properties. A cytoplasmic scFv antibody was employed, for example, in order to modulate the activity of the phytochrome A protein in genetically modified tobacco plants (Owen, 1992, Bio/Technology 10, 790-794; Review: Franken et al., 1997, Current Opinion in Biotechnology 8; 411-416; Whitelam, 1996, Trends Plant Sci. 1, 268-272).

In general, every promoter active in plant cells is suitable for the expression of the foreign nucleic acid molecule/polynucleotide (the foreign nucleic acid molecules/polynucleotides). The promoter can thus be selected in such a way that the expression occurs constitutively in the plants of the invention or only in a certain tissue, at a certain time in the plant's development or at a time determined by external factors. With regard to the plant, the promoter can be homologous or heterologous.

Suitable promoters for the expression of nucleic acids/polynucleotides that reduce the activity of a target gene, are, for example, the cauliflower mosaic virus 35S RNA promoter and the ubiquitin promoter from maize for a constitutive expression, the patatin gene promoter B33 (Rocha-Sosa et al., 1989, EMBO J. 8, 23-29), the MCPI promoter of the metal-locarboxypeptidase inhibitor gene from potato (HU 9801674) or the GBSSI promoter from potato (WO 92/11376) for a tuber-specific expression in potato plants or a promoter that ensures that expression only occurs in photo-synthetically active tissues, e.g. the ST-LS1 promoter (Stockhaus et al., 1987, Proc. Natl. Acad. Sci. USA 84, 7943-7947; Stockhaus et al., 1989, EMBO J. 8, 2445-2451), the Ca/b promoter (for example see U.S. Pat. No. 5,656,496; U.S. Pat. No. 5,639,952; Bansal et al., 1992, Proc. Natl. Acad. Sci. USA 89, 3654-3658) and the rubisco SSU promoter (for example see U.S. Pat. No. 5,034,322; U.S. Pat. No. 4,962, 028) or, for an endosperm-specific expression, the glutelin promoter (Leisy et al., 1990, Plant. Mol. Biol. 14, 41-50; Zheng et al., 1993, Plant. J. 4, 357-366; Yoshihara et al., 1996, FEBS Lett. 383, 213-218), the Shrunken-1 promoter (Werr et al., 1985, EMBO J. 4, 1373-1380), the HMG promoter from wheat, the USP promoter, the phaseolin promoter or promoters from zein genes from maize (Pedersen et al., 1982, Cell 29, 1015-1026; Quatroccio et al., 1990, Plant Mol. Biol. 15, 81-93).

Preferred promoters for the expression of the foreign nucleic acid molecule/polynucleotide (foreign nucleic acid molecules/polynucleotides) are the patatin gene, the MCPI promoter and the GBSSI promoter from potato.

The expression of the foreign nucleic acid molecule/polynucleotide (foreign nucleic acid molecules/polynucleotides) is particularly beneficial in starch-storing organs of the plant. Such organs are, for example, the tubers of the potato plant or the granules or the endosperm of maize, wheat or rice plants. Therefore, promoters are preferably used, which cause expression in these organs.

However, promoters can also be used that are only activated by external factors at a determined time (e.g. see WO 93/07279). Promoters of heat-shock proteins that allow a simple induction can be of particular interest in this regard. In addition, seed-specific promoters can be used, such as the USP promoter from *Vicia faba*, for example, which allows for seed-specific expression in *Vicia faba* and other plants (Fiedler et al., 1993, Plant Mol. Biol. 22, 669-679; Bäumlein et al., 1991, Mol. Gen. Genet. 225, 459-467) as well as fruit-specific promoters, such as those described, for example, in WO 91/01373.

Furthermore, a termination sequence that serves to terminate correctly the transcription as well as to add a poly(A) tail onto the transcript can be present, and which is ascribed the function of stabilising the transcripts. These types of elements are described in literature (e.g. see Gielen et al., 1989, EMBO J. 8, 23-29) and are freely exchangeable.

There are numerous techniques available for introducing DNA into a plant host cell. These techniques include the transformation of plant cells with T-DNA using *Agrobacterium tumefaciens* or *Agrobacterium rhizogenes* as a transformation agent, the fusion of protoplasts, the injection and electroporation of DNA, the insertion of DNA using the biolistic approach and other possibilities.

The use of *Agrobacteria*-mediated transformation of plant cells has been intensively researched and is adequately described in EP-A 0120516 and by Hoekema (1985, The Binary Plant Vector System, Offsetdrukkerij Kanters B. V., Alblasserdam, Chapter V), Fraley et al. (Crit. Rev. Plant. Sci. 4, 1-46) and An et al. (1985, EMBO J. 4, 277-287). For the transformation of potato plants, see, for example, Rocha-Sosa et al., 1989, EMBO J. 8, 29-33.

The transformation of monocotyledonous plants with vectors based on *Agrobacterium* transformation has also been described (Chan et al., 1993, Plant. Mol. Biol. 22, 491-506; Hiei et al., 1994, Plant J. 6, 271-282; Deng et al., 1990, Science in China 33, 28-34; Wilmink et al., 1992, Plant Cell Reports 11, 76-80; May et al., 1995, Bio/Technology 13, 486-492; Conner and Domisse, 1992, Int. J. Plant Sci. 153, 550-555; Ritchie et al., 1993, Transgenic Res. 2, 252-265). Alternative means for the transformation of monocotyledonous plants are transformation using the biolistic approach (Wan and Lemaux, 1994, Plant Physiol. 104, 37-48; Vasil et al., 1993, Bio/Technology 11, 1553-1558; Ritala et al., 1994, Plant Mol. Biol. 24, 317-325; Spencer et al., 1990, Theor. Appl. Genet. 79, 625-631), protoplast transformation, electroporation of partially permeabilised cells and insertion of DNA using glass fibres. In particular, the transformation of maize has been described several times in literature (e.g. see WO 95/06128, EP-A 0513849, EP-A 0465875, EP-A 0292435; Fromm et al., 1990, Biotechnology 8, 833-844; Gordon-Kamm et al., 1990, Plant Cell 2, 603-618; Koziel et al., 1993, Biotechnology 11, 194-200; Moroc et al., 1990, Theor. Appl. Genet. 80, 721-726).

The successful transformation of other types of cereal has been described as well, for example for barley (Wan and Lemaux, supra; Ritala et al., supra; Krens et al., 1982, Nature 296, 72-74) and for wheat (Nehra et al., 1994, Plant J. 5, 285-297).

A further subject matter of the present invention is a genetically plant cell in which the genetic modification leads to a reduction in the GBSSI, SSIII and BEI activities relative to the GBSSI, SSIII and BEI activity in corresponding wild type plant cells or wild type plants, and which contains at least one foreign nucleic acid selected from the group consisting of:
- a) polynucleotides that code for at least one antisense RNA, which leads to a reduction in the expression of at least one endogenous GBSSI gene and/or to a reduction in the expression of at least one endogenous SSIII gene and/or to a reduction in the expression of at least one endogenous BEI gene;
- b) polynucleotides, which, through a cosuppression effect, lead to a reduction in the expression of at least one endogenous GBSSI gene and/or to a reduction in the expression of at least one endogenous SSIII gene and/or to a reduction in the expression of at least one endogenous BEI gene;
- c) polynucleotides that code for at least one ribozyme, which specifically cleaves transcripts of at least one endogenous GBSSI gene and/or of at least one SSIII gene and/or of at least one BEI gene;
- d) polynucleotides introduced by in vivo mutagenesis that lead to a mutation or an insertion in at least one endogenous GBSSI gene and/or to a mutation or an insertion in at least one endogenous SSIII gene and/or to a mutation or an insertion in at least one endogenous BEI gene, whereby the mutation or insertion leads to a reduction in the expression of the said gene or to the synthesis of inactive GBSSI and/or inactive SSIII and/or inactive BEI;
- e) polynucleotides that code for at least one antisense RNA and at least one sense RNA, whereby the said antisense RNA and sense RNA can form a double-stranded RNA molecule that leads to a reduction in the expression of at least one endogenous GBSSI gene and/or to a reduction in the expression of at least one endogenous SSIII gene and/or to a reduction in the expression of at least one endogenous BEI gene;
- f) polynucleotides that contain transposons, whereby the integration of the transposon sequences leads to a mutation or an insertion in at least one endogenous GBSSI gene and/or to a mutation or an insertion in at least one endogenous SSIII gene and/or to a mutation or an insertion in at least one endogenous BEI gene, whereby the mutation or insertion leads to a reduction in the expression of the said gene or to the synthesis of inactive GBSSI and/or inactive SSIII and/or inactive BEI;
- g) T-DNA molecules, which, through insertion into at least one endogenous GBSSI gene and/or insertion into at least one endogenous SSIII gene and/or insertion in at least one endogenous BEI gene, lead to a reduction in the expression of the said gene or to the synthesis of inactive GBSSI and/or inactive SSIII and/or inactive BEI.

An additional subject matter of the present invention is any type of propagation material of plants of the invention.

The plant cells of the invention can be used for the regeneration of entire plants.

The plants, obtainable by way of regeneration of the plant cells of the invention, are a further subject matter of the present invention.

The plants of the invention or the plant cells of the invention can belong to any optional plant species, i.e. both monocotyledonous and dicotyledonous plants. Preferably they are agricultural crops, i.e. plants that are cultivated by people for the purposes of nutrition or for technical, in particular industrial purposes and their cells. The invention preferably relates to fibre-producing plants (e.g. flax, hemp, cotton), oil-storing plants (e.g. rapeseed, sunflower, Soya bean), sugar-storing plants (e.g. sugar-beet, sugar cane, sugar sorghum) and protein-storing plants (e.g. legumes) and their cells.

In another preferred embodiment, the invention relates to forage crops, particularly forage and pasture grasses (alfalfa, clover, etc.) and vegetable plants (e.g. tomato, lettuce, chicory) and their cells.

In another preferred embodiment, the invention relates to starch-storing plants (e.g. wheat, barley, oats, rye, potato, maize, rice, pea, cassava), more preferred potato, and their cells.

The term "potato" as mentioned herein refers to plants and tubers, respectively, of the species *Solanum* (*tuberosum*).

The plant cells of the invention or the plants of the invention produce a starch that exhibits changed physico-chemical properties in comparison to starch from wild type plant cells or plants, particularly with regard to the amylose content, the amylopectin content or the amylose/amylopectin ratio, the phosphate content, the viscosity behaviour, the DSC peak temperature, the side chain distribution, the freeze/thaw stability, the heat stability and/or the gel solidity, so that the starch is better suited for special applications.

Surprisingly, it was found that the composition of the starch produced by the plant cells of the invention or the plants of the invention is changed, among other things, such that it exhibits an amylose content of less than 10% by weight, an increased phosphate content, an increased gelatinisation temperature, an unchanged or slightly decreased DSC peak temperature, an altered amylopectin side chain distribution, a high freeze/thaw stability, a high heat stability, a decreased minimum viscosity, a decreased end viscosity, an increased viscostability (stability of viscosity) and/or a decreased gel solidity in comparison to starch from wild type plant cells or plants.

Furthermore, it was surprisingly found that the starch produced by the plant cells of the invention or the plants of the invention exhibits a higher peak temperature in the DSC analysis in comparison to other starches with a comparable phosphate content.

The starches of the invention exhibit properties that make them seem particularly suitable for use in processes in which high swellability, a high freeze/thaw stability and/or a high charge density are advantageous. These requirements apply to thickening agents in the food industry, particularly if they are frozen for storage or processing and/or a particularly high thickening capacity is desirable. The starches of the invention also exhibit properties in comparison to customary starches which make them seem advantageous for use in the area of bread improvers as well as fillings and crèmes. With regard to bread improvers, improvement in water retention, delay in the ageing of the bread and the improved freeze/thaw stability play a large role; with respect to fillings and crèmes, the high transparency of the starch gels is advantageous as well. A further area of application for the starches of the invention is in meat products, where the improved properties with respect to water retention ability, high freeze/thaw stability and low gelatinisation temperature are particularly important.

Furthermore, the starches of the invention are particularly well suited for use in the paper industry owing to their high charge density, high viscostability and low viscosity thickening. The high charge density is particularly beneficial since it enables frequently used amphoteric starches to be produced in a single-step derivatisation reaction. In addition, the starches of the invention are particularly well suited for use in the area of adhesives owing to their viscous properties.

The plant cells of the invention or the plants of the invention produce a starch with an amylose content of less than 10% by weight.

In a preferred embodiment of the invention, the plant cells of the invention or the plants of the invention produce a starch with an amylose content of less than 5% by weight, particularly preferably less than 2% by weight.

In conjunction with the present invention, the amylose content is determined by the method of Hovenkamp-Hermelink et al. (1988, Potato Research 31, 241-246) described below for potato starch. This method is also applicable to starches isolated from other plant species. Methods for the isolation of starches are known to the person skilled in the art.

The plant cells of the invention or the plants of the invention produce a starch with an increased phosphate content relative to starch from respective wild type plant cells or wild type plants.

In conjunction with the present invention, the term "increased phosphate content" means that the phosphate content is increased at the C6-position of the starch produced by the plant cells of the invention or the plants of the invention, particularly by at least 200%, preferably by at least 250%, more preferably by at least 300% relative to starch from corresponding wild type plant cells or wild type plants. The phosphate content at the C6-position of the starch produced by the plant cells of the invention or the plants of the invention is increased, particularly by 200%-400%, preferably by 300%-400% and more preferably by 350%-380% relative to starch from corresponding wild type plant cells or wild type plants.

In conjunction with the present invention, the term "phosphate content at the C6-position" is to be understood to mean the content of phosphate groups that are bonded to the carbon atom at position 6 of the glucose monomers of the starch. Fundamentally, the C2, C3 and C6 positions of the glucose units in the starch can be phosphorylated in vivo. In conjunction with the present invention, the determination of the phosphate content at the C6-position (=C6-P content) is carried out by means of a glucose-6-phosphate analysis with the optical enzymatic test described below (Nielsen et al., 1994, Plant Physiol. 105, 111-117).

In a preferred embodiment of the invention, the starch produced by the plant cells of the invention or the plants of the invention exhibits a phosphate content in the C6-position of 30-100 nmol C6-P per mg of starch, more preferably 35-80 nmol C6-P per mg of starch, and most preferably 40-60 nmol C6-P per mg of starch.

In further preferred embodiment of the invention, the starch produced by the plant cells of the invention or the plants of the invention exhibit a phosphate content in the C6-position of at least 30 nmol C6-P per mg of starch, preferably at least 35 nmol C6-P per mg of starch, and more preferably at least 40 nmol C6-P per mg of starch.

In particular, the plant cells of the invention or the plants of the invention produce a starch with a higher gelatinisation temperature (RVA PT) in comparison to other starches with a comparable phosphate content.

In conjunction with the present invention, the term "higher gelatinisation temperature (RVA PT)" means that the gelatinisation temperature (RVA PT) according to RVA analyses as per the method described below is increased by 0.5° C.-4° C., particularly by 1° C.-3° C., in comparison to the gelatinisation temperature RVA PT of starch from corresponding wild type plant cells or wild type plants.

In particular, the starch produced by the plant cells of the invention or the plants of the invention exhibit a gelatinisation temperature RVA PT of >65° C., preferably of 65.5° C.-70° C. and more preferably of 66° C.-68° C.

It was surprising to the person skilled in the art that the gelatinisation temperature RVA PT of the starch produced by the plant cells of the invention or the plants of the invention is increased in comparison to the gelatinisation temperature RVA PT of starch from corresponding wild type plant cells or wild type plants, for starches that have a phosphate content comparable to the starches of the invention are usually characterised by a significant decrease (3°-4° C.) in the gelatinisation temperature RVA PT.

This property of the starch of the invention is first and foremost a considerable advantage in all processes for which a high viscostability is desirable. This applies to processes in the paper industry, for example, where sometimes high flow rates must be obtained, and also in other process in which starches are transported as pastes. On account of its viscosity behaviour, use of the starch of the invention is particularly advantageous in the textile industry, especially where low-viscosity to soluble starches are used.

In particular, the plant cells of the invention and the plants of the invention produce a starch with an unchanged or slightly decreased DSC peak temperature Tp in comparison to starch from corresponding wild type plant cells or wild type plants.

In conjunction with the present invention, the term "slightly decreased DSC peak temperature Tp" means a reduction of a maximum of 3° C. and in particular a maximum of 1.5° C. in comparison to the DSC peak temperature of starch from corresponding wild type plant cells or wild type plants. In conjunction with the present invention, the determination of the DSC peak temperature Tp is carried out by the method described below ("DSC measurement").

The starch produced by the plant cells of the invention and the plants of the invention typically exhibits a DSC peak temperature Tp of >65° C., preferably of 66° C.-70° C., and more preferably of 67° C.-68.5° C.

It was surprising to the person skilled in the art that the DSC peak temperature of the starch of the invention is not decreased considerably more in comparison to the DSC peak temperature of starch from corresponding wild type plant cells or wild type plants. This is because starches that have a comparable phosphate content to the starches of the invention are usually characterised by a considerable decrease (approx. 7° C.) in the DSC peak temperature.

Native starches with a high degree of phosphorylation normally lose their crystallinity at considerably lower temperature than comparable starches with a lower phosphate content. In many thermal processes and applications the use of granular starches with a concomitant high water retention ability or swellability is desirable. The surprisingly high DSC peak temperature or the surprisingly high gelatinisation temperature in the RVA of the starches of the invention are therefore particularly beneficial, since it enables the structure of the starch granules to be maintained at elevated process temperatures.

In particular, the plant cells of the invention or the plants of the invention produce a starch with an altered side chain distribution in comparison to starch from corresponding wild type plant cells or wild type plants.

In conjunction with the present invention, the term "altered side chain distribution" means an increase in the fraction of short side chains of amylopectin with a DP (=degree of polymerisation) of 6 by at least 100%, preferably by at least 200% and more preferably by at least 250% in comparison to the fraction of short side chains with a DP of 6 of amylopectin from corresponding wild type plant cells or wild type plants and/or a reduction in the fraction of short side chains with a DP of 8-9 by at least 15%, preferably by at least 25% and more preferably by at least 35% in comparison to the fraction of short side chains with a DP of 8-9 of amylopectin from corresponding wild type plant cells or wild type plants and/or an increase in the fraction of short side chains with a DP of 30-4 by 5%-40%, preferably by 10%-30% and more preferably by 15%-25% in comparison to the fraction of short side chains with a DP 30-34 of amylopectin from corresponding wild type plant cells or wild type plants.

In conjunction with the present invention, the determination of the side chain distribution is carried out by the method described below ("Analysis of Amylopectin Side Chain Distribution by Ion Exchange Chromatography"). The determination of the fraction of short side chains is carried out by determining the fraction of a specific side chain expressed as a percentage of all side chains. The total fraction of all side chains is calculated by determining the total area under the peaks which represent polymerisation grades of DP 6 to 34 in the HPLC chromatogram. The fraction of a specific side chain expressed as a percentage of all side chains is calculated by determining the ratio of the area under the peak which represents this side chain in the HPLC chromatogram, to the entire area. The Chromelion 6.20 program by the Dionex Company, USA, can be used, for example, for determining the peak areas.

In particular the plant cells of the invention or the plants of the invention produce a starch with a high freeze/thaw stability.

In conjunction with the present invention, the term "high freeze/thaw stability" means a freeze/thaw stability of at least 60%, preferably at least 70%, more preferably at least 80% and most preferably at least 95%. In conjunction with the present invention, determination of the freeze/thaw stability is carried out by the method described below.

In particular, the plant cells of the invention or the plants of the invention produce a starch with a high heat stability.

In conjunction with the present invention, the term "high heat stability" means a heat stability of at least 30%, preferably at least 40% and more preferably at least 50%. In conjunction with the present invention, determination of the heat stability occurs is carried out by the method described below.

In particular, the plant cells of the invention or the plants of the invention particularly produce a starch with a decreased minimum viscosity (RVA Min) and a decreased end viscosity (RVA Fin) in comparison to starch from corresponding wild type plant cells or wild type plants.

In conjunction with the present invention, the term "decreased minimum viscosity (RVA Min)" means that the measured value for the minimum viscosity (RVA Min) by RVA analyses by means of the method described below is a maximum of 55%, preferably a maximum of 50% and more preferably a maximum of 40%, of the measured value determined for starch from corresponding wild type plant cells or wild type plants. The "RVA Min" value measured for the starch produced by the plant cells of the invention or the plants of the invention lies in particular between 30% and 55%, preferably between 30% and 50% and more preferably between 30% and 45% of the measured value determined for starch from corresponding wild type cells or wild type plants.

In conjunction with the present invention, the term "decreased end viscosity (RVA Fin)" means that the value measured for the end viscosity (RVA Fin) by RVA analyses by means of the method described below is a maximum of 65%, preferably a maximum of 60% and more preferably a maximum of 50%, of the value measured for starch from corresponding wild type plant cells or wild type plants. The "RVA Fin" value measured for the starch produced by the plant cells of the invention or the plants of the invention lies in particular between 30% and 65%, preferably between 30% and 60%, more preferably between 30% and 55% and most preferably between 30% and 50%, of the value measured for starch from corresponding wild type plant cells or wild type plants.

In particular, the plant cells of the invention or the plants of the invention particularly produce a starch with a higher viscostability in comparison to starch from corresponding wild type plant cells or wild type plants.

In conjunction with the present invention, the term "higher viscostability" means that the "RVA Set" value determined for the starch produced by the plant cells of the invention or the plants of the invention, i.e. the difference of the "RVA Fin" value and the "RVA Min" value, is lower than the corresponding value determined for starch from corresponding wild type plant cells or wild type plants. In particular, the "RVA Set" value is reduced by at least 10%.

In particular, the plant cells of the invention or the plants of the invention particularly produce a starch with decreased gel solidity in comparison to starch from corresponding wild type plant cells or wild type plants.

In conjunction with the present invention, the term "decreased gel solidity" means that the gel solidity is decreased by at least 70%, particularly by at least 80% and preferably by at least 90%, in comparison to the gel solidity of starch from corresponding wild type plant cells or wild type plants. The gel solidity of the starch produced by the plant cells of the invention or the plants of the invention lies in particular between 60% and 95%, preferably between 70% and 95% and more preferably between 80% and 95% in comparison to the gel solidity of starch from corresponding wild type plant cells or wild type plants. In conjunction with the present invention, the determination of the gel solidity is carried out with the aid of a texture analyser under the conditions described below.

A further subject matter of the present invention is the starch produced by the plant cells of the invention or the plants of the invention with one or more of the properties described above. That is, this description of the invention discloses any combination of the following starch properties: amylose content or amylose/amylopectin ratio, phosphate content, gelatinisation temperature, DSC peak temperature, side chain distribution, freeze/thaw stability, heat stability, minimum viscosity, end viscosity and gel solidity. All combinations of two, three, four, five, six, seven, eight, nine and all properties are to be considered disclosed.

The starch is preferably potato starch.

The starches of the invention can be subsequently modified by methods known to the person skilled in the art.

It is known to the person skilled in the art that the properties of starch can be altered by using, for example, thermal, chemical, enzymatic or mechanical derivatisation. Derivatised starches are particularly suited for many different applications. The starches of the invention are better suited than customary starches to be starting materials for the production of derivatised starches because they have a higher proportion of reactive functional groups owing to the higher starch phosphate content, and because the starch of the invention exhibits a higher gelatinisation temperature or melting temperature than starches with a comparable phosphate content.

Therefore, a further subject matter of the present invention is methods for the production of a derivatised starch in which starch of the invention is subsequently modified.

In conjunction with the present invention, the term "derivatised starch" means a starch of the invention, the properties of which have been altered with the aid of chemical, enzymatic, thermal or mechanical methods after being isolated from plant cells.

In particular, the derivatised starch of the invention is a starch treated with heat and/or acid.

In a further embodiment the derivatised starches are starch ethers, particularly starch alkyl ethers, O-allyl ethers, hydroxyalkyl ethers, O-carboxymethyl ethers, nitrogen-containing starch ethers, phosphate-containing starch ethers or sulphur-containing starch ethers.

In a further embodiment the derivatised starches are cross-linked starches.

In a further embodiment the derivatised starches are starch graft polymers.

In a further embodiment the derivatised starches are oxidised starches.

In a further embodiment the derivatised starches are starch esters, particularly starch esters that were introduced into the starch with the use of organic acids. These are more preferably phosphate, nitrate, sulphate, xanthate, acetate or citrate starches.

The derivatised starches of the invention are suitable for various applications in the pharmaceutical industry, the food industry and/or the non-food industry. Methods for the production of derivatised starches of the invention are known to the person skilled in the art and are adequately described in general literature. A review of the production of derivatised starches has been published, for example, by Orthoefer (in Corn, Chemistry and Technology, 1987, Eds. Watson and Ramstad, Chapter 16, 479-499).

A further subject matter of the present invention is derivatised starches that are obtainable by the method of the invention for the production of a derivatised starch.

A further subject matter of the present invention is the use of starches of the invention for the production of derivatised starches.

The starches of the invention are suitable for various applications in the food and non-food industries in modified or unmodified form.

The opportunities for the use for the starch can be divided fundamentally into two large areas. The one area encompasses the hydrolysis products of the starch, mainly glucose and glucan components, which are obtained by means of enzymatic or chemical methods. They serve as starting materials for additional chemical modifications and processes such as fermentation. Simplicity and the ability to perform the hydrolysis process in cost-effective manner can be important for achieving a reduction in costs. In general process is currently carried out enzymatically with the use of amyloglucosidase. Cost savings through the decreased use of enzymes is conceivable. This can be achieved by a change in the starch structure, e.g. enlargement of the surface area of the granules, easier digestibility by a decrease in the degree of branching or a steric structure that limits accessibility for the enzymes employed.

The second area, in which the starch is used as a so-called native starch owing to its polymeric structure, is subdivided into two further areas of application:

1. Food Industry

Starch is a classic additive for many foods, in which it fundamentally takes on the function of binding aqueous additives, or effects an increase in viscosity or an increase in gel formation. Important fundamental properties are the flow and absorption behaviour, the swelling temperature and gelatinisation temperature, the viscosity and thickening capacity, the starch solubility, the transparency and paste structure, the heat stability, shear stability and acid stability, the retrogradation tendency, the film formation ability, the freeze/thaw stability, the digestibility and the ability to form complexes, for example, with inorganic or organic ions.

2. Non-Food Industry

In this large area the starch can be used as an auxiliary in various production processes or as an additive in technical products. The use of starch as an auxiliary in the paper and cardboard industry is of particular note. In this field, the starch is used mainly for retardation (retention of solids), for setting filler and fine particles, as a solidifying substance and for dehydration. Moreover, the favourable properties of the starch with regard to stiffness, hardness, sound, grip, gloss, smoothness, tear strength as well as the surfaces are utilised.

2.1 Paper and Cardboard Industries

Within the paper production process, a differentiation can be made between four fields of application, namely surface, coating, mass and spraying.

In the wet end starch is added to the pulp in order to improve the strength of paper. The starch is bound by electrostatic interactions to the fibre by using a fixative. High charge density, good solubility and high viscosity are important characteristics for a good performance. The demands on starch with regard to surface sizing applications are essentially a high degree of brightness, appropriate viscosity, high viscostability, good film formation, low dust formation as well as retainability due to anionic charges. When used in coating applications, the solid content, an appropriate viscosity, a high bonding ability as well as a high pigment affinity play an important role. For coating applications the starch can be modified to the right viscosity level and can be used in high concentrations. Viscostability and retainability due the presence of anionic charges are important characteristics for a good performance. An amylopectin starch with increased bound phosphate combines both required functionalities. As an additive to the mass, rapid, uniform, loss-free distribution, high mechanical stability and complete retention in the paper pulp are of importance. When using the starch in spraying applications, an appropriate solid content, fast swelling, high viscosity and high bonding ability are also significant for optimal binding power.

2.2 Adhesives Industry

A major field of application is in the adhesives industry, where the fields of application are subdivided into four areas: use as pure starch glue, use in starch glues prepared with special chemicals, the use of starch as an additive to synthetic resins and polymer dispersions and the use of starches as extenders for synthetic adhesives. 90% of all starch-based adhesives are used in the production of corrugated board, paper sacks and bags, composite materials for paper and aluminium, boxes and re-wettable glue for envelopes, stamps, etc.

2.3 Textile and Textile Care Products Industries

Another large area of use for starches is as auxiliaries and additives in the production of textiles and textile care products. Within the textile industry, a differentiation can be made between the following four fields of application: the use of starch as a sizing agent, i.e. as an auxiliary for smoothing and strengthening the burring behaviour for protection against tractive forces present in weaving as well as for the increase of wear resistance during weaving, as an agent for textile improvement mainly after quality-deteriorating pre-treatments, such as bleaching, dying, etc., as a thickener in the production of dye pastes for the prevention of dye diffusion and as an additive to chaining agents for sewing yarns.

2.4 Building Industry

The fourth area of use for starches is as an additive in building materials. One example is the production of gypsum plasterboards, in which the starch mixed in the thin plaster pastifies with the water, diffuses to the surface of the gypsum board and thus binds the cardboard to the board. Other fields of application are to the admixture with plaster and mineral fibres. In ready-mixed concrete, starch products are used for the retardation of the setting process.

2.5 Ground Stabilisation

An additional market for starch is the production of agents for ground stabilization for use in the temporary protection of ground particles against water in artificial earth shifting. According to state-of-the-art knowledge combination products consisting of starch and polymer emulsions can be considered to have the same erosion- and encrustation-reducing effect as the products hitherto used, but are considerably less expensive.

2.6 Use in Plant Protection Agents and Fertilisers

A field of application is the use of starch in plant protection agents for modification of the specific properties of these preparations. For instance, starches are used for improving the wetting of plant protection agents and fertilisers, for the regulated release of the active ingredients, for the conversion of liquid, volatile and/or malodorous active ingredients into microcrystalline, stable, ductile substances, for mixing incompatible compounds and for the prolongation of the duration of the effect by reduction in degradation.

2.7 Pharmaceuticals, Medicine and Cosmetics Industry

A further area of use is in the fields of pharmaceuticals, medicine and in the cosmetics industry. In the pharmaceutical industry the starch may be used as a binder for tablets or for the dilution of the binder in capsules. Furthermore, starch is suitable as a disintegrant for tablets since, upon swallowing, it absorbs fluid and after a short time it swells so much that the active ingredient is released. For qualitative reasons, medicinal powder lubricants and wound powders are based on starch. In the field of cosmetics, the starch may be used, for example, as a support for powder additives such as scents and salicylic acid. A relatively extensive field of application for starch is toothpaste.

2.8 Starch as an Additive in Coal and Briquettes

One area of use for starch is as an additive in coal and briquettes. By adding starch, coal can be quantitatively agglomerated and/or briquetted at a high quality, thus preventing premature disintegration of the briquettes. Barbecue charcoal contains between 4 and 6% added starch, calorated coal between 0.1 and 0.5%. Furthermore, the starch is suitable as a binding agent since adding it to coal and briquette can considerably reduce the emission of toxic substances.

2.9 Processing of Ore and Coal Slurry

The starch can additionally be used as a flocculant for the processing of ore and coal slurry.

2.10 Additive for Casting Materials

Another field of application is the use as an additive to auxiliaries in casting. In numerous casting processes cores produced from sands mixed with binding agents are needed. Nowadays, the most commonly used binding agent is bentonite mixed with modified starches, mostly swelling starches.

The purpose of adding starch is to increase flow resistance and to improve binding strength. Moreover, swelling starches may fulfil more prerequisites for the production process, such as dispersability in cold water, rehydratability, good mixability in sand and high water retention capacity.

2.11 Use in the Rubber Industry

In the rubber industry starch may be used for improving the technical and optical quality. Reasons for this are: improved surface gloss, grip and appearance. For this purpose, the starch is dispersed on the sticky rubberised surfaces of rubber substances before the cold vulcanisation. It may also be used for improving the printability of rubber.

2.12 Use as an Additive in Boring

A further possible area of use for the starches of the invention is in the extraction of raw materials with borers. For example, when extracting crude oil it is necessary to employ auxiliaries and/or lubricants to prevent the borer or borer rod from overheating.

2.13 Production of Leather Substitutes

Another field of application for the modified starches is the production of leather substitutes.

2.14 Starch in Synthetic Polymers

In the plastics sector the following fields of application stand out: the integration of products derived from starch into the processing process (starch is only a filler, there is no direct bond between synthetic polymer and starch) or, alternatively, the integration of products derived from starch into the production of polymers (starch and polymer form a stable bond).

The use of the starch as a pure filler cannot compete with other substances such as talc. This situation is different when the specific starch properties become effective and the property profile of the end products is thus clearly changed. One example is the use of starch products in the processing of thermoplastic materials, such as polyethylene. Thereby, starch and the synthetic polymer are combined in a ratio of 1:1 by means of coexpression to form a "master batch", from which various products are produced by means of conventional techniques using granulated polyethylene. With the incorporation of starch into polyethylene films an increased freeness in hollow bodies, improved water vapour permeability, improved antistatic behaviour, improved anti-block behaviour as well as improved printability with aqueous dyes can be achieved.

Another possibility is the use of the starch in polyurethane foams. With the adaptation of starch derivatives and the optimisation of processing techniques it is possible to control specifically the reaction between synthetic polymers and the hydroxy groups of the starches. The results arising from the use of starch are polyurethane films with the following property profiles: a reduced coefficient of thermal expansion, decreased shrinking behaviour, improved pressure/stress behaviour, increased water vapour permeability without a change in water absorption, reduced flammability and cracking density, no dripping of combustible parts, no halides and reduced aging. Disadvantages that currently still exist are reduced pressure and impact strength.

Product development is no longer limited only to films. Solid plastics products, such as pots, plates and bowls can also be produced with of a starch content of more than 50%. Furthermore, the starch/polymer mixtures offer the advantage that they are much more readily biodegradable.

Furthermore, owing to their extreme capability to bind water, starch graft polymers have gained considerably in importance. These are products with a backbone of starch and a side lattice of a synthetic monomer grafted on using the principle of radical chain mechanism. The starch graft polymers currently available are characterised in that they have an improved binding and retention capacity of up to 1000 g water per g starch at a high viscosity. The scope for these superabsorbers has increased considerably in recent years and lies in the hygiene sector with products such as nappies and bed sheets, and in the agriculture sector, e.g. seed pelleting.

Pivotal for the use of the novel starch are, on the one hand, structure, water content, protein content, lipid content, fibre content, ash/phosphate content, amylose/amylopectin ratio, distribution of the relative molar mass, degree of branching, granule size and shape as well as crystallinity, and on the other hand, the properties that lead into the following features: flow and sorption behaviour, gelatinisation temperature, viscosity, thickening performance, solubility, paste structure, transparency, heat, shear and acid resistance, tendency to retrogradation, gel formation performance, freeze/thaw stability, complex formation performance, iodine bonding, film formation, adhesive strength, enzyme stability, digestibility and reactivity.

General Methods

The following methods were used in the examples:

Method for the Extraction of Starch from Potatoes

All tubers of a line (4 to 5 kg) were processed together in a commercially available juicer (Multipress automatic MP80, Braun). The starch-containing juice from the tubers was collected in a 10 l bucket which contained 200 ml tap water and a teaspoon (approx. 3-4 g) sodium disulphite. The bucket was then completely filled with tap water. After the starch had settled for 2 hours, the supernatant was decanted off, and the starch was again suspended in 10 l tap water and filtered through a sieve with 125 μm mesh size. After two hours (the starch had once again settled on the bottom of the bucket) the aqueous supernatant was decanted once more. This washing procedure was repeated three further times so that the starch was re-suspended in fresh tap water a total of five times. Finally, the starches were dried at 37° C. to a water content of 12-17% and homogenised in a mortar. The starches were then available for analyses.

Starch Analysis a) Determination of the Amylose/Amylopectin Ratio

Starch was isolated from potato plants by standard methods (see above), and the ratio of amylose to amylopectin was determined by the method described by Hovenkamp-Hermelink et al. (1998, Potato Research 31, 241-246).

b) Determination of the Phosphate Content

The C2, C3 and C6 positions of the glucose units in the starch can be phosphorylated. In order to determine the C6-P content of the starch, 50 mg starch were hydrolysed in 500 μl 0.7 M HCl for four hours at 95° C. Subsequently, the preparations were centrifuged for 10 min at 15500 g and the supernatants were removed. Alliquots of 7 μl of the supernatants were mixed with 193 μl imidazole buffer (100 mM imidazole, pH 7.4; 5 mM $MgCl_2$, 1 mM EDTA and 0.4 mM NAD). The measurement was conducted at 340 nm using a photometer. After establishing the base-line absorption, the enzyme reaction was started by adding 2U glucose-6-phosphate dehydrogenase (from Leuconostoc mesenteroides, Boehringer Mannheim). The change in absorption is directly proportional to the concentration of G-6-P of the starch.

c) Determination of Viscosity Properties with a Rapid Visco Analyser (RVA)

The viscosity properties were determined by the method described in WO 01/19975.

2 g starch (TS) were taken up into 25 ml $H_2O$ (deionised water, conductivity of at least 15 M Ohm) and analysed in a Rapid Visco Analyser (Newport Scientific Pty Ltd., Investment Support Group, Warriewod NSW 2102, Australia) for the determination of viscosity properties. The device was operated according to the manufacturer's instructions. In order to determine the viscosity of the aqueous starch solution, the starch suspension was first stirred for 10 sec at 960 rpm (revolutions per minute), and subsequently heated for 1 min at 50° C. at an agitation speed of 160 rpm (Step 1). The temperature was then raised from 50° C. to 95° C. at a temperature gradient of 12° C. per min while maintaining the same agitation speed (Step 2). The temperature was maintained at 95° C. for 2.5 min at the same agitation speed (Step 3). The solution was then cooled from 95° C. to 50° C. at a cooling rate of 12° C. per min while maintaining the same agitation speed (Step 4). The final step (Step 5) involved holding the temperature steady at 50° C. for 2 min while maintaining the same agitation speed. The viscosity was determined for the whole duration of the process.

After concluding the programme, the stirrer was removed and the beaker was covered. The gelatinisation starch was then available for texture analysis after 24 hours.

In the RVA analysis profile, there are characteristic values that are displayed for the comparison of different measurements and substances. In conjunction with the present invention, the following terms are to be understood as follows:

1. Maximum Viscosity (RVA Max)

The maximum viscosity is understood to be the highest viscosity value, measured in cP (centipoises), that is attained in Step 2 or 3 of the temperature profile.

2. Minimum Viscosity (RVA Min)

The minimum viscosity is understood to be the lowest viscosity value, measured in cP, that occurs after the maximum viscosity in the temperature profile. This normally takes place in Step 3 of the temperature profile.

3. Final Viscosity (RVA Fin)

The final viscosity is understood to be the viscosity value, measured in cP, that occurs at the end of the measurement.

4. Setback (RVA Set)

The so-called "setback" is calculated by subtracting the minimum viscosity value from the final viscosity value.

5. Gelatinisation Temperature (RVA PT)

The gelatinisation temperature is understood to be the time in the temperature profile, in which the viscosity first rises by 55 cP over a period of 20 sec.

d) Determination of the Gel Solidity (Texture Analyser)

2 g starch (TS) were gelatinised in 25 ml of an aqueous suspension in the RVA device (temperature program: see c) "Determination of Viscosity Properties using a Rapid Visco Analyser (RVA)") and subsequently stored in a closed container for 24 hours at room temperature.

The samples were fixed under the probe (cylindrical plunger with planar surface) of a TA-XT2 texture analyser of the Stable Micro Systems Company (Surrey, UK) and the gel solidity was determined with the following parameters:

| | |
|---|---|
| Test Speed | 0.5 mm/sec |
| Penetration Depth | 7 mm |
| Contact Surface | 113 $mm^2$ |
| Pressure | 2 g | e) Analysis of the Amylopectin Side Chain Distribution by Ion Exchange Chromatography In order to separate amylose and amylopectin 200 mg starch were dissolved in 50 ml reaction vessels with 12 ml 90% (v/v) DMSO in $H_2O$. After adding 3 volumes of ethanol the precipitate was separated by centrifugation for 10 min at approx. 1800 g at room temperature (RT). The pellet was then washed with 30 ml ethanol, dried and dissolved in 40 ml 1% (w/v) NaCl solution at 75° C. After cooling the solution to 30° C. 90 mg thymol were added slowly and this solution was incubated for at least 60 hours at 30° C. The solution was then centrifuged for 30 min at 2000 g (RT). The supernatant was treated with 3 volumes of ethanol and the precipitated amylopectin was separated by centrifugation for 5 min at 2000 g (RT). The pellet (amylopectin) was then washed with ethanol and dried with acetone. Next, a 1% amylopectin solution in 10 mM sodium acetate, pH 3.5, was produced in which the amylopectin was dissolved at 65-95° C. for 1-2 hours. In each case 100 µl of this solution were treated with 180 µl 10 mM sodium acetate, pH 3.5, and 1 µl isoamylase (Megazyme), for digestion, and the preparations were incubated at 37° C. for approximately 16 hours. An aqueous 1:5 dilution of the digestion product was then filtered with an 0.2 µm filter, and 100 µl of the filtrate was analysed by ion chromatography (HPAEC-PAD, Dionex). The separation was carried out with a PA-100 column (with a corresponding pre-column), and the detection was conducted amperometrically.

The elution conditions were as follows:

| t (min) | Solution A (%) | Solution B (%) |
|---------|----------------|----------------|
| 5       | 0              | 100            |
| 35      | 30             | 70             |
| 45      | 32             | 68             |
| 60      | 100            | 0              |
| 70      | 100            | 0              |
| 72      | 0              | 100            |
| 80      | 0              | 100            |
| Stop    |                |                |

Solution A - 0.15 M NaOH
Solution B - 1 M sodium acetate in 0.15 M NaOH

The determination of the relative ratio of short side chains to the total amount of all side chains was carried out by determining the percentage ratio of a specific side chain to the total amount of all side chains. The total amount of all detectable side chains was calculated by determining the total area under the peaks that represents the degree of polymerisation of DP 6 up to 34 in the HPCL chromatogram.

The percentage ratio of a specific side chain to the total amount of all side chains was calculated by determining the ratio of the peak area that represents this side chain in the HPLC chromatogram to the entire area. The Chromelion 6.20 programme Version 6.20 by the Dionex Company, USA, was used for determining the peak areas.

f) Analysis of the Side Chain Distribution of the Total Starch Using Gel Permeation Chromatography In order to determine the side chain distribution of the total starch with gel permeation chromatography, 10 mg starch were dissolved in 250 µl 90% (v/v) DMSO at 60° C. for approx. 3 hours. After the addition of 375 µl $H_2O$ (distilled), the solution was heated at 95° C. for approximately 1 hour.

For digestion 200 µl starch solution were added to 300 µl 16.6 mM sodium acetate, pH 3.5, and the preparation was incubated at 37° C. for approximately 16 hours with 2 µl isoamylase (Megazyme). An aqueous 1:4 dilution of the digestion product was then filtered with a 0.2 µm filter, and 25 µl of the filtrate was analysed using gel permeation chromatography.

The separation was carried out with two columns connected in series. First, a Gram 3000 column (Polymer Standards Service, with corresponding pre-column) followed by a Gram 100 column. The detection was carried out with a refractive index detector (RI 71, Shodex). The column was equilibrated with 90% (v/v) DMSO, 90 mM sodium acetate. It was eluted with 90% (v/v) DMSO, 90 mM sodium acetate at a flow rate of 0.7 ml/min over a period of one hour.

In order to correlate the elution volume with the molar mass, the columns used were calibrated with dextran standards. The dextrans used, their corresponding molar mass and the elution volumes are presented in Table 7. By means of the calibration lines obtained the elution diagram was illustrated as molecular weight distribution. (Appendix, Table 10).

g) Determination of the Freeze/Thaw Stability

In order to determine the freeze/thaw stability, 3.5 g starch (dry weight) were mixed with 70 ml distilled water and gelatinised in a rotation viscosimeter (Rotovisko, Haake) at 90° C. for 15 min (128 rpm, inclined blade mixer). The starch paste was then autoclaved in a glass with a screw cap for 15 min at 121° C. Then in each case 5 g of the paste were subjected three times to a freeze/thaw cycle (from room temperature to −20° C.), also in a glass with a screw top. This preparation was then treated with 25 ml distilled water, homogenised in an Ultra-Turrax at 8000 rpm for 1 min and finally extracted at 37° C. in a drying cabinet on a magnet stirrer for one hour. The sample was then transferred into a 50 ml graduated flask, distilled water was added until the sample totaled 50 ml, and the preparation was centrifuged at 2800 g for 5 min and filtered. An aliquot of this filtrate was evaporated over night at 105° C. and the residue weighed. The freeze/thaw stability was then determined as follows:

$$\text{Freeze/Thaw Stability (\%)} = \frac{50 \times 100 \times TS \text{ in the balance pan (g)}}{\text{Aliquot(g)} \times \text{Starch } TS \text{ of the sample (g)}}$$

h) Determination of the Heat Stability

In order to determine the heat stability, 3.5 g starch (dry weight) were mixed with distilled water to make 70 ml and gelatinised in a rotation viscosimeter (Rotovisko, Haake) at 90° C. for 15 min (128 rpm, inclined blade mixer). Next, the starch paste were autoclaved in a glass with a screw cap for 15 min at 121° C. and then returned to the rotation viscosimeter beaker.

After 6 min at 90° C. and 128 rpm with the inclined blade mixer, the scale divisions are read, and the value expressed as a ratio with the value measured after 21 min at 128 rpm and 90° C., without autoclaving.

$$\text{Heat Stability(\%)} = \frac{\text{Scale divisions (after autoclaving)} \times 100}{\text{Scale divisions (21 min, 128 rpm, 90° C.)}}$$

i) DSC Measurement (Differential Scanning Calorimetry)

The DSC measurement was carried out by the method described in WO 01/19975. 10 mg starch were weighed into a stainless steel pan (volume 50 µl) with 30 µl distilled water. The sample was heated from 20° C. to 150° C. in a Diamond DSC apparatus (Perkin Elmer) at a temperature gradient of 10° C./min. The data analysis was performed using a software programme by Pyres.

EXAMPLE 1

Production of Transgenic Potato Plants that Exhibit Reduced BEI, SSIII and GBSSI Gene Expression For the production transgenic plants that exhibit reduced BEI, SSIII and GBSSI activity, transgenic plants that exhibit reduced BEI and SSIII activity are first produced. For this purpose T-DNA of the pB33-aBEI-aSSIII-kan plasmid was transferred into potato plants with the aid of *Agrobacteria* as described by Rocha-Sosa et al. (1989, EMBO J. 8, 23-29).

For the construction of the pB33-aBEI-aSSIII-kan plasmid, the pBin33-kan expression vector was first constructed. For this purpose, the promoter of the patatin gene B33 from *Solanum tuberosum* (Rocha-Sosa et al., 1989, supra) was inserted as a DraI fragment (nucleotides −1512 to +14) into the pUC19 vector (Genbank Acc. No. M77789) cut with SstI, the ends of which had been blunt-ended with the aid of the T4-DNA polymerase. This gave the pUC19-B33 plasmid. The B33 promoter was excised from this plasmid with EcoRI and SmaI and inserted into the correspondingly excised pBinAR vector. This created the pBin33-kan plant expression vector. The pBinAR plasmid is a derivative of the pBin19 vector plasmid (Bevan, 1984, Nucl. Acid Research 12, 8711-8721) and was constructed by Höfgen and Willmitzer (1990, Plant Sci. 66, 221-230). Next, a 1631 Bp long HindIII fragment, which contains a partial cDNA coding for BEI from potato (Kossmann et al., 1991, Mol. Gen. Genet. 230 (1-2), 39-44), was blunt-ended and inserted into the pBinB33 vector, which had previously been cleaved with SmaI, in an "antisense" orientation with respect to the B33 promoter (promoter of the patatin gene B33 from *Solanum tuberosum*; Rocha-Sosa et al., 1989, supra). The resulting plasmid was cleaved using BamHI. A 1363 Bp long BamHI fragment containing a partial cDNA coding for SSIII from potato (Abel et al., 1996, supra) was inserted into the incision, also in an "antisense" orientation with respect to the B33 promoter.

In order to detect the activity of soluble starch synthases by non-denaturing gel electrophoresis tissue samples of potato tubers were digested in 50 mM Tris-HCl pH 7.6, 2 mM DTT, 2.5 mM EDTA, 10% glycerol and 0.4 mM PMSF. The electrophoresis was conducted in a MiniProtean II chamber (Bio-RAD). The monomer concentration of the 1.5 mm thick gels was 7.5% (w/v). 25 mM Tris-Glycine pH 8.4 served as the gel buffer and running buffer. Equal quantities of protein extract were applied and separated for 2 hours at 10 mA per gel.

Next, the activity gels were incubated in 50 mM Tricine-NaOH pH 8.5, 25 mM potassium acetate, 2 mM EDTA, 2 mM DTT, 1 mM ADP glucose, 0.1% (w/v) amylopectin and 0.5 M sodium citrate. Glucans formed were stained with Lugol's solution.

The detection of BEI activity was also carried out by non-denaturing gel electrophoresis: the sample material was ground with a mortar and pestle in liquid nitrogen in order to isolate proteins from plants, it was then taken up into extraction buffer (50 mM Na-citrate, pH 6.5; 1 mM EDTA, 4 mM DTT), centrifuged (10 min, 14000 g, 4° C.) and directly measured for protein concentration as described by Bradford. Afterward, 5 to 20 µg total protein extract, as needed, was mixed with 4× loading buffer (20% glycerol, 125 mM Tris-HCl, pH 6.8) and loaded on a "BE activity gel". The running buffer (RB) was comprised of the following: RB=30.2 g Tris-base, pH 8.0, 144 g glycine to 1 l H$_2$O.

After the gel run was concluded the gels were each incubated overnight at 37° C. in 25 ml "phosphorylase buffer" (25 ml 1M Na-citrate pH 7.0, 0.47 g glucose-1-phosphate, 12.5 mg AMP, 2.5 mg phosphorylase a/b from rabbits). The gel staining was carried out with Lugol's solution.

Various lines of transgenic potato plants could be identified, the tubers of which exhibit clearly reduced BEI and SSIII activity. The line whose isolated starches exhibited the highest phosphate content of all independent transformants examined (asBEI-asSSIII) was subsequently transformed with the p35SaGBSSI-met plasmid as described by Rocha-Sosa et al., (1989, EMBO J. 8, 23-29).

The p35SaGBSSI-met plasmid was produced by inserting a 1921 Bp long Asp718/XbaI fragment containing a partial cDNA coding for GBSSI from potato (Hergersberg, 1988, supra) in an "antisense" orientation with respect to the 35S promoter into the similarly opened pBinAR-met vector.

The pBinAR-met vector is based on the pGPTV-DHFR vector, which is a derivative of the pBin19 vector (Becker et al., 1992, Plant Mol. Biol. 20, 1195-1197). pBinAR-met contains the dhfr gene instead of the nptII gene, which provides resistance against methotrexate, as well as the 3'-end of the 7 gene of the T-DNA of the Ti plasmid pTiACH5 (Nucleotides 2106-2316; Gielen et al., 1984, EMBO J. 3, 835-846) instead of the 3'-end of the nopaline synthase gene. Starting from the pA7 plasmid (see the pBinAR vector description above), the EcoRI-HindIII fragment including the 35S promoter, the ocs terminator and the part of the polylinker lying in between were inserted into the correspondingly cleaved pGPTV-DHFR plasmid. The resulting vector was designated as pBinAR-met.

Tissue samples from the tubers of the independent transformants were taken from the plants obtained from transformation with the p35SaBGSSI-met plasmid, which were designated as asBEI-asSSIII-asGBSSI plants, and the samples were then stained with iodine solution and examined under the microscope. The starches of the independent lines whose granules were stained brown were removed for further analysis of the starch properties.

EXAMPLE 2

Analysis of Starch from Plants with Reduced BEI, SSII and GBSSI Gene Expression

The starches of various independent lines of the transformation asBEI-asSSIII-asGBSSI described in Example 1, were isolated from potato tubers that had been produced outdoors in 2002. Next, the physico-chemical properties of these starches were analysed. The results obtained from starches produced on the basis of the plant cells of the invention or plants of the invention are indicated in the following tables, either as absolute values or as a percentage ratio relative to starch from corresponding wild type plant cells or wild type plants (henceforth called "WT starch"). In addition, the tables contain starch data from "single" and "double" combinations from WO 00/08184 and WO 01/12782:

TABLE 1

| | % Relative to WT Starch | | |
|---|---|---|---|
| | Phosphate in C6 | Amylose | Gel Solidity |
| asSSIII | 197 | 123 | 84 |
| cosSSIII | 210 | — | 83 |
| asBEI | 170 | 91 | 91 |
| asGBSSI | 110 | <18 | — |
| asBEI-asSSIII | 292 | — | 100 |
| asGBSSI-asBEI | 181 | <18 | 21 |
| asBEI-asSSIII-asGBSSI | 360 | <18 | 16 |

TABLE 2

| | % Relative to WT Starch | | | | |
|---|---|---|---|---|---|
| Preparation | RVA Max | RVA Min | RVA Fin | RVA Set | RVA PT |
| asSSIII | 82 | 75 | 76 | 79 | 95 |
| cosSSIII | 100 | 60 | 70 | 74 | 95 |
| asBEI | 124 | 94 | 90 | 76 | 100 |
| asGBSSI | 70 | 90 | 84 | 57 | 104 |
| asBEI-asSSIII | 128 | 69 | 75 | 97 | 95 |
| asGBSSI-asBEI | 69 | 84 | 78 | 51 | 102 |
| asBEI-asSSIII-asGBSSI | 74 | 38 | 46 | 84 | 103 |

TABLE 2-continued

| Preparation | % Relative to WT Starch | | | | |
|---|---|---|---|---|---|
| | RVA Max | RVA Min | RVA Fin | RVA Set | RVA PT |

Legend for Table 1 and Table 2:
RVA = Rapid Visco Analyser,
RVA Max = maximum viscosity,
RVA Min = minimum viscosity,
RVA Fin = viscosity at the end of the measurement,
RVA Set = setback = difference between RVA Fin and RVA min,
RVA PT = gelatinisation temperature.

TABLE 3

| Genotype | C6-Phosphate [nmol/mg] | Absolute Amylose [%] | RVA Max [cP] | RVA Min [cP] | RVA Fin [cP] | RVA Set [cP] | RVA PT [°C.] | Gel Solidity [g] |
|---|---|---|---|---|---|---|---|---|
| Desiree (Wild Type) | 12.1 | 24.1 | 7494 | 2332 | 2860 | 528 | 64.9 | 19.2 |
| asBEI-asSSIII-asGBSSI | 43.5 | <3 | 5524 | 875 | 1317 | 442 | 66.5 | 3.1 |

Table 3: RVA values (method as described in WO 01/19975), amylose content, phosphate content in the C6-position and gel solidity of the starch from the asBEI-asSSIII-asGBSSI are absolute. Legend: RVA=Rapid Visco Analyser, RVA Max=maximum viscosity, RVA Min=minimum viscosity, RVA Fin=viscosity at the end of the measurement, RVA Set=setback=difference between RVA Fin and RVA Min, RVA PT=gelatinisation temperature.

Analyses by DSC measurements ("differential scanning calorimetry") were conducted by the method described in WO 01/19975. For comparison, additional potato starches were included that exhibit an increase in the phosphate content (asBEI-asSSIII line) and a decrease in the amylose content ("waxy" potato starch, asGBSSI line).

TABLE 4

| Line | $T_P$ in °C. | dH in J/g | $T_P$ in % relative to WT Starch | dH in % relative to WT Starch |
|---|---|---|---|---|
| asBEI-asSSIII-asBGSSI | 68.08 | 22.37 | 98.8 | 93.4 |
| Desiree (Wild Type) | 68.90 | 23.95 | | |
| asBEI-asSSIII | 62.03 | 21.11 | 89.9 | 93.6 |
| Desiree (Wild Type) | 69.00 | 22.56 | | |
| asGBSSI | 72.29 | 24.92 | 102.7 | 113.8 |
| Desiree (Wild Type) | 70.37 | 21.91 | | |

Table 4: Results of the DSC analysis. Tp=peak temperature in °C., dH=melting enthalpy in J/g starch.

The analysis of the amylopectin side chain distribution was conducted as described above. The following table (Table 5) contains an overview of the ratio of the area of the individual peaks in the HPAEC chromatogram to the total peak area for WT starch (from Desiree) and starch from the asBEI-asSSIII-asGBSSI line:

TABLE 5

| Glucose Units | WT Starch | asBEI-asSSIII-asGBSSI |
|---|---|---|
| dp6 | 1.24 | 3.39 |
| dp7 | 1.25 | 1.14 |
| dp8 | 1.32 | 0.79 |
| dp9 | 3.11 | 1.92 |
| dp10 | 4.35 | 3.09 |
| dp11 | 5.49 | 4.36 |
| dp12 | 6.23 | 5.46 |
| dp13 | 6.5 | 6.17 |
| dp14 | 6.41 | 6.29 |
| dp15 | 6.06 | 5.99 |
| dp16 | 5.7 | 5.5 |
| dp17 | 5.22 | 5.03 |
| dp18 | 4.86 | 4.7 |
| dp19 | 4.64 | 4.59 |
| dp20 | 4.39 | 4.46 |
| dp21 | 4.15 | 4.2 |
| dp22 | 3.8 | 3.95 |
| dp23 | 3.49 | 3.63 |
| dp24 | 3.17 | 3.35 |
| dp25 | 2.86 | 3.12 |
| dp26 | 2.62 | 2.88 |
| dp27 | 2.33 | 2.63 |
| dp28 | 2.04 | 2.35 |
| dp29 | 1.77 | 2.07 |
| dp30 | 1.54 | 1.81 |
| dp31 | 1.3 | 1.57 |
| dp32 | 1.11 | 1.37 |
| dp33 | 0.9 | 1.13 |
| dp34 | 0.75 | 0.94 |

TABLE 6

| Glucose Units | asBEI-asSSIII-asGBSSI [% relative to WT Starch] |
|---|---|
| dp6 | 273.39 |
| dp7 | 91.20 |
| dp8 | 59.85 |
| dp9 | 61.74 |
| dp10 | 71.03 |
| dp11 | 79.42 |
| dp12 | 87.64 |
| dp13 | 94.92 |
| dp14 | 98.13 |
| dp15 | 98.84 |
| dp16 | 96.49 |
| dp17 | 96.36 |
| dp18 | 96.71 |
| dp19 | 98.92 |
| dp20 | 101.59 |
| dp21 | 101.20 |
| dp22 | 103.95 |
| dp23 | 104.01 |
| dp24 | 105.68 |

TABLE 6-continued

| Glucose Units | asBEI-asSSIII-asGBSSI [% relative to WT Starch] |
|---|---|
| dp25 | 109.09 |
| dp26 | 109.92 |
| dp27 | 112.88 |
| dp28 | 115.20 |
| dp29 | 116.95 |
| dp30 | 117.53 |
| dp31 | 120.77 |
| dp32 | 123.42 |
| dp33 | 125.56 |
| dp34 | 125.33 |

Table 6: Change in each individual peak surface area relative to WT starch, expressed as a percentage.

A more detailed analysis of the side chain profile, but for the total starch (amylose was not previously separated as was the case in the HPAEC analysis), was carried out by determining the percentage ratio of a specific group of side chains to the total quantity of side chains in a GPC chromatogram. For this purpose, the entire area of the GPC chromatogram was subdivided into individual section, which represent the corresponding groups of side chains of various lengths. The selected sections contain side chains with the following degree of polymerisation (dp=quantity of glucose monomers within a side chain): dp<12, dp12-19, dp20-25, dp26-31, dp32-37, dp38-43, dp44-49, dp50-56, dp57-62, dp63-123 and dp>123. In order to correlate the elution volume with the molar mass, the GPC column used is calibrated with dextran standards (Fluka, Product #31430). The dextrans used, their respective molar mass and the elution volumes are shown in Table 7. The resulting calibration lines are used to create the elution diagram, which shows the molecular weight distribution (Appendix, Table 10). A molecular weight of 162 was set for glucose for the purpose of calculating a molecular weight of the individual side chains. The entire surface area in the GPC chromatogram is taken to be 100%, and the parts of the area representing the individual sections are calculated as a percentage of the entire area.

TABLE 7

| Elution Volume | Molar Mass [D] | Sample Name |
|---|---|---|
| 18.76 | 401300 | Dextran T670 |
| 19.41 | 276500 | Dextran T410 |
| 20.49 | 196300 | Dextran T270 |
| 21.35 | 123600 | Dextran T150 |
| 22.45 | 66700 | Dextran T80 |
| 23.52 | 43500 | Dextran T50 |

TABLE 7-continued

| Elution Volume | Molar Mass [D] | Sample Name |
|---|---|---|
| 25.15 | 21400 | Dextran T25 |
| 26.92 | 9890 | Dextran T12 |
| 28.38 | 4440 | Dextran T5 |
| 30.77 | 1080 | Dextran T1 |

Table 7: Calibration Table with Dextran Standards

TABLE 8

| Degree of Polymerisation (dp) | W(log M) | | | % with respect to WT Starch | |
|---|---|---|---|---|---|
| | WT | asBEI-asSSIII | asBEI-asSSIII-asGBSSI | asBEI-asSSIII | asBEI-asSSIII-asGBSSI |
| dp < 12 | 4.03 | 4.83 | 6.31 | 119.71 | 156.57 |
| dp12-19 | 13.66 | 14.19 | 16.26 | 103.83 | 119.00 |
| dp20-25 | 13.14 | 15.81 | 17.32 | 120.36 | 131.79 |
| dp26-31 | 10.83 | 13.79 | 15.40 | 127.31 | 142.19 |
| dp32-37 | 6.79 | 8.33 | 9.79 | 122.60 | 144.16 |
| dp38-43 | 5.28 | 5.44 | 6.86 | 103.14 | 130.00 |
| dp44-49 | 4.34 | 3.62 | 4.99 | 83.42 | 114.95 |
| dp50-56 | 4.49 | 3.26 | 4.80 | 72.51 | 106.85 |
| dp57-62 | 4.34 | 2.99 | 4.57 | 68.85 | 105.21 |
| dp63-123 | 14.10 | 7.96 | 12.94 | 56.44 | 91.78 |
| dp > 123 | 18.99 | 19.78 | 0.75 | 104.21 | 3.97 |

Table 8: Distribution of the side chain profile of the total starch from the asBEI-asSSIII, asBEI-asSSIII-asGBSSI lines and the corresponding wild type starch, divided into groups with various degrees of polymerisation.

Furthermore, the freeze/thaw stability and the heat stability were determined for the starch from the asBEI-asSSIII-asGBSSI lines and for the corresponding wild type starch.

TABLE 9

| Line | Freeze/Thaw Stability (%) | Heat Stability (%) |
|---|---|---|
| Wild Type (Desiree) | 9.4 | 25 |
| asBEI-asSSIII-asGBSSI | 96.9 | 56 |

Table 9: Freeze/Thaw stability and heat stability of starch from the asBEI-asSSIII-asGBSSI line and of the corresponding wild type starch.

APPENDIX TABLE 10

Distribution of the side chain profile of the total starch from the asBEI-asSSIII, asBEI-asSSIII-asGBSSI lines and from the corresponding wild type starch, without division into groups according to various degrees of polymerisation.

| Molar Mass (D) | W (log M) | | | % of the Total Area | | |
|---|---|---|---|---|---|---|
| | WT | asBEIasSSIII | asBEIasSSIII asGBSSI | WT | asBEIasSSIII | asBEIasSSIII asGBSSI |
| 964.429 | 0.000 | 0.000 | 0.000 | 0.000 | 0.000 | 0.000 |
| 994.426 | 0.000 | 0.000 | 0.014 | 0.000 | 0.000 | 0.018 |
| 1025.360 | 0.000 | 0.000 | 0.021 | 0.000 | 0.000 | 0.028 |
| 1057.250 | 0.000 | 0.000 | 0.034 | 0.000 | 0.000 | 0.045 |
| 1090.130 | 0.000 | 0.000 | 0.038 | 0.000 | 0.000 | 0.050 |
| 1124.040 | 0.000 | 0.000 | 0.051 | 0.000 | 0.000 | 0.068 |

APPENDIX TABLE 10-continued

Distribution of the side chain profile of the total starch from the asBEI-asSSIII, asBEI-asSSIII-asGBSSI lines and from the corresponding wild type starch, without division into groups according to various degrees of polymerisation.

| Molar Mass (D) | W (log M) | | | % of the Total Area | | |
|---|---|---|---|---|---|---|
| | WT | asBEIasSSIII | asBEIasSSIII asGBSSI | WT | asBEIasSSIII | asBEIasSSIII asGBSSI |
| 1159.000 | 0.000 | 0.001 | 0.058 | 0.000 | 0.002 | 0.077 |
| 1195.050 | 0.000 | 0.019 | 0.074 | 0.000 | 0.025 | 0.099 |
| 1232.220 | 0.000 | 0.033 | 0.082 | 0.000 | 0.043 | 0.109 |
| 1270.540 | 0.000 | 0.048 | 0.102 | 0.001 | 0.064 | 0.136 |
| 1310.060 | 0.019 | 0.064 | 0.110 | 0.026 | 0.085 | 0.147 |
| 1350.810 | 0.032 | 0.086 | 0.129 | 0.043 | 0.114 | 0.172 |
| 1392.820 | 0.061 | 0.105 | 0.136 | 0.081 | 0.140 | 0.181 |
| 1436.150 | 0.085 | 0.126 | 0.168 | 0.113 | 0.168 | 0.223 |
| 1480.810 | 0.111 | 0.143 | 0.185 | 0.147 | 0.191 | 0.246 |
| 1526.870 | 0.128 | 0.175 | 0.216 | 0.171 | 0.232 | 0.287 |
| 1574.360 | 0.152 | 0.195 | 0.242 | 0.202 | 0.259 | 0.322 |
| 1623.330 | 0.182 | 0.223 | 0.270 | 0.242 | 0.296 | 0.359 |
| 1673.820 | 0.212 | 0.252 | 0.294 | 0.282 | 0.335 | 0.391 |
| 1725.880 | 0.246 | 0.275 | 0.323 | 0.327 | 0.366 | 0.430 |
| 1779.560 | 0.283 | 0.304 | 0.361 | 0.377 | 0.404 | 0.481 |
| 1834.910 | 0.314 | 0.335 | 0.396 | 0.417 | 0.446 | 0.526 |
| 1891.990 | 0.358 | 0.374 | 0.439 | 0.476 | 0.497 | 0.583 |
| 1950.830 | 0.399 | 0.418 | 0.482 | 0.531 | 0.557 | 0.641 |
| 2011.510 | 0.449 | 0.452 | 0.520 | 0.597 | 0.602 | 0.691 |
| 2074.080 | 0.498 | 0.498 | 0.578 | 0.663 | 0.662 | 0.770 |
| 2138.590 | 0.556 | 0.535 | 0.631 | 0.739 | 0.712 | 0.839 |
| 2205.100 | 0.604 | 0.585 | 0.692 | 0.804 | 0.778 | 0.921 |
| 2273.690 | 0.654 | 0.632 | 0.752 | 0.870 | 0.840 | 1.000 |
| 2344.410 | 0.699 | 0.700 | 0.821 | 0.930 | 0.931 | 1.092 |
| 2417.330 | 0.753 | 0.753 | 0.874 | 1.002 | 1.002 | 1.163 |
| 2492.510 | 0.803 | 0.814 | 0.945 | 1.068 | 1.083 | 1.258 |
| 2570.040 | 0.857 | 0.872 | 1.006 | 1.140 | 1.160 | 1.338 |
| 2649.980 | 0.897 | 0.939 | 1.068 | 1.193 | 1.249 | 1.421 |
| 2732.400 | 0.937 | 0.996 | 1.132 | 1.247 | 1.325 | 1.507 |
| 2817.390 | 0.968 | 1.060 | 1.192 | 1.288 | 1.411 | 1.586 |
| 2905.020 | 1.007 | 1.116 | 1.241 | 1.340 | 1.485 | 1.651 |
| 2995.370 | 1.040 | 1.165 | 1.288 | 1.383 | 1.550 | 1.714 |
| 3088.540 | 1.063 | 1.212 | 1.334 | 1.414 | 1.613 | 1.774 |
| 3184.600 | 1.081 | 1.251 | 1.372 | 1.438 | 1.664 | 1.825 |
| 3283.650 | 1.091 | 1.287 | 1.415 | 1.451 | 1.712 | 1.883 |
| 3385.780 | 1.101 | 1.314 | 1.437 | 1.465 | 1.748 | 1.912 |
| 3491.090 | 1.102 | 1.343 | 1.459 | 1.466 | 1.786 | 1.942 |
| 3599.680 | 1.110 | 1.356 | 1.483 | 1.476 | 1.804 | 1.973 |
| 3711.640 | 1.110 | 1.369 | 1.492 | 1.477 | 1.821 | 1.985 |
| 3827.080 | 1.118 | 1.375 | 1.508 | 1.487 | 1.830 | 2.007 |
| 3946.120 | 1.102 | 1.381 | 1.515 | 1.466 | 1.837 | 2.016 |
| 4068.850 | 1.093 | 1.375 | 1.503 | 1.453 | 1.830 | 2.000 |
| 4195.410 | 1.073 | 1.363 | 1.503 | 1.428 | 1.813 | 1.999 |
| 4325.900 | 1.059 | 1.336 | 1.484 | 1.408 | 1.777 | 1.975 |
| 4460.450 | 1.034 | 1.319 | 1.470 | 1.376 | 1.755 | 1.955 |
| 4599.180 | 1.010 | 1.290 | 1.450 | 1.344 | 1.716 | 1.929 |
| 4742.230 | 0.986 | 1.268 | 1.420 | 1.312 | 1.686 | 1.889 |
| 4889.730 | 0.956 | 1.226 | 1.392 | 1.272 | 1.631 | 1.852 |
| 5041.820 | 0.932 | 1.188 | 1.354 | 1.239 | 1.581 | 1.801 |
| 5198.640 | 0.909 | 1.152 | 1.322 | 1.210 | 1.532 | 1.760 |
| 5360.330 | 0.881 | 1.104 | 1.285 | 1.172 | 1.469 | 1.710 |
| 5527.060 | 0.862 | 1.068 | 1.253 | 1.147 | 1.421 | 1.668 |
| 5698.970 | 0.838 | 1.020 | 1.204 | 1.115 | 1.357 | 1.602 |
| 5876.220 | 0.811 | 0.983 | 1.169 | 1.079 | 1.307 | 1.555 |
| 6058.990 | 0.805 | 0.934 | 1.126 | 1.071 | 1.242 | 1.498 |
| 6247.450 | 0.797 | 0.896 | 1.091 | 1.060 | 1.192 | 1.452 |
| 6441.760 | 0.796 | 0.853 | 1.063 | 1.059 | 1.134 | 1.414 |
| 6642.120 | 0.788 | 0.815 | 1.027 | 1.048 | 1.084 | 1.367 |
| 6848.710 | 0.788 | 0.784 | 1.007 | 1.049 | 1.043 | 1.339 |
| 7061.730 | 0.800 | 0.745 | 0.970 | 1.065 | 0.991 | 1.290 |
| 7281.370 | 0.801 | 0.718 | 0.958 | 1.065 | 0.955 | 1.274 |
| 7507.850 | 0.818 | 0.682 | 0.944 | 1.088 | 0.907 | 1.255 |
| 7741.370 | 0.817 | 0.672 | 0.931 | 1.086 | 0.894 | 1.239 |
| 7982.150 | 0.827 | 0.649 | 0.917 | 1.100 | 0.864 | 1.220 |
| 8230.420 | 0.833 | 0.631 | 0.913 | 1.108 | 0.840 | 1.215 |
| 8486.410 | 0.843 | 0.617 | 0.896 | 1.121 | 0.821 | 1.193 |
| 8750.370 | 0.855 | 0.601 | 0.901 | 1.137 | 0.800 | 1.199 |
| 9022.530 | 0.845 | 0.597 | 0.895 | 1.124 | 0.795 | 1.191 |
| 9303.160 | 0.840 | 0.587 | 0.885 | 1.117 | 0.782 | 1.177 |
| 9592.520 | 0.815 | 0.574 | 0.875 | 1.083 | 0.764 | 1.164 |

APPENDIX TABLE 10-continued

Distribution of the side chain profile of the total
starch from the asBEI-asSSIII, asBEI-asSSIII-asGBSSI lines and from
the corresponding wild type starch, without division into groups
according to various degrees of polymerisation.

| | W (log M) | | | % of the Total Area | | |
|---|---|---|---|---|---|---|
| Molar Mass (D) | WT | asBEIasSSIII | asBEIasSSIII asGBSSI | WT | asBEIasSSIII | asBEIasSSIII asGBSSI |
| 9890.880 | 0.814 | 0.551 | 0.843 | 1.083 | 0.733 | 1.121 |
| 10198.500 | 0.797 | 0.535 | 0.832 | 1.060 | 0.712 | 1.107 |
| 10515.700 | 0.769 | 0.523 | 0.800 | 1.023 | 0.695 | 1.064 |
| 10842.800 | 0.742 | 0.512 | 0.777 | 0.987 | 0.682 | 1.033 |
| 11180.000 | 0.713 | 0.493 | 0.741 | 0.948 | 0.656 | 0.985 |
| 11527.800 | 0.688 | 0.460 | 0.700 | 0.915 | 0.612 | 0.931 |
| 11886.300 | 0.653 | 0.439 | 0.673 | 0.869 | 0.584 | 0.895 |
| 12256.000 | 0.639 | 0.403 | 0.624 | 0.850 | 0.536 | 0.830 |
| 12637.200 | 0.594 | 0.381 | 0.594 | 0.790 | 0.507 | 0.791 |
| 13030.300 | 0.564 | 0.351 | 0.554 | 0.750 | 0.467 | 0.737 |
| 13435.600 | 0.538 | 0.328 | 0.512 | 0.715 | 0.436 | 0.682 |
| 13853.500 | 0.516 | 0.292 | 0.472 | 0.686 | 0.388 | 0.628 |
| 14284.400 | 0.496 | 0.256 | 0.433 | 0.660 | 0.341 | 0.576 |
| 14728.700 | 0.457 | 0.245 | 0.401 | 0.609 | 0.326 | 0.534 |
| 15186.800 | 0.430 | 0.210 | 0.372 | 0.571 | 0.280 | 0.495 |
| 15659.100 | 0.407 | 0.190 | 0.337 | 0.542 | 0.253 | 0.448 |
| 16146.200 | 0.388 | 0.166 | 0.302 | 0.516 | 0.221 | 0.401 |
| 16648.400 | 0.365 | 0.142 | 0.270 | 0.486 | 0.188 | 0.359 |
| 17166.200 | 0.326 | 0.133 | 0.254 | 0.434 | 0.176 | 0.338 |
| 17700.100 | 0.317 | 0.118 | 0.227 | 0.421 | 0.157 | 0.302 |
| 18250.600 | 0.279 | 0.109 | 0.210 | 0.371 | 0.146 | 0.279 |
| 18818.300 | 0.266 | 0.082 | 0.178 | 0.354 | 0.109 | 0.237 |
| 19403.600 | 0.240 | 0.079 | 0.160 | 0.319 | 0.105 | 0.213 |
| 20007.100 | 0.213 | 0.070 | 0.139 | 0.284 | 0.094 | 0.185 |
| 20629.400 | 0.190 | 0.051 | 0.122 | 0.253 | 0.067 | 0.162 |
| 21271.100 | 0.166 | 0.053 | 0.115 | 0.221 | 0.071 | 0.153 |
| 21932.700 | 0.159 | 0.040 | 0.088 | 0.211 | 0.053 | 0.117 |
| 22614.800 | 0.134 | 0.029 | 0.078 | 0.178 | 0.039 | 0.104 |
| 23318.200 | 0.118 | 0.026 | 0.051 | 0.157 | 0.035 | 0.068 |
| 24043.500 | 0.104 | 0.020 | 0.042 | 0.139 | 0.026 | 0.056 |
| 24791.300 | 0.089 | 0.027 | 0.038 | 0.118 | 0.036 | 0.050 |
| 25562.400 | 0.074 | 0.014 | 0.020 | 0.098 | 0.018 | 0.027 |
| 26357.500 | 0.068 | 0.011 | 0.014 | 0.091 | 0.015 | 0.018 |
| 27177.300 | 0.057 | 0.011 | 0.000 | 0.076 | 0.014 | 0.000 |
| 28022.600 | 0.046 | 0.013 | | 0.061 | 0.017 | |
| 28894.200 | 0.034 | 0.013 | | 0.045 | 0.017 | |
| 29792.900 | 0.037 | 0.005 | | 0.049 | 0.007 | |
| 30719.600 | 0.027 | 0.011 | | 0.036 | 0.014 | |
| 31675.000 | 0.030 | 0.008 | | 0.040 | 0.010 | |
| 32660.200 | 0.024 | 0.010 | | 0.032 | 0.013 | |
| 33676.100 | 0.018 | 0.018 | | 0.024 | 0.024 | |
| 34723.500 | 0.019 | 0.014 | | 0.026 | 0.019 | |
| 35803.500 | 0.008 | 0.018 | | 0.010 | 0.024 | |
| 36917.100 | 0.018 | 0.011 | | 0.025 | 0.014 | |
| 38065.400 | 0.014 | 0.019 | | 0.019 | 0.025 | |
| 39249.300 | 0.013 | 0.033 | | 0.018 | 0.045 | |
| 40470.100 | 0.013 | 0.027 | | 0.017 | 0.036 | |
| 41728.900 | 0.001 | 0.027 | | 0.002 | 0.036 | |
| 43026.800 | 0.017 | 0.024 | | 0.022 | 0.031 | |
| 44365.100 | 0.018 | 0.025 | | 0.024 | 0.033 | |
| 45745.000 | 0.015 | 0.028 | | 0.020 | 0.037 | |
| 47167.800 | 0.011 | 0.027 | | 0.014 | 0.036 | |
| 48634.800 | 0.013 | 0.038 | | 0.018 | 0.050 | |
| 50147.500 | 0.010 | 0.022 | | 0.014 | 0.029 | |
| 51707.300 | 0.019 | 0.041 | | 0.026 | 0.054 | |
| 53315.600 | 0.018 | 0.034 | | 0.024 | 0.046 | |
| 54973.900 | 0.016 | 0.036 | | 0.021 | 0.047 | |
| 56683.700 | 0.015 | 0.040 | | 0.020 | 0.053 | |
| 58446.800 | 0.018 | 0.029 | | 0.024 | 0.039 | |
| 60264.700 | 0.016 | 0.036 | | 0.022 | 0.048 | |
| 62139.100 | 0.026 | 0.039 | | 0.034 | 0.051 | |
| 64071.800 | 0.023 | 0.046 | | 0.030 | 0.062 | |
| 66064.700 | 0.014 | 0.045 | | 0.019 | 0.060 | |
| 68119.500 | 0.023 | 0.045 | | 0.030 | 0.059 | |
| 70238.200 | 0.017 | 0.055 | | 0.022 | 0.073 | |
| 72422.900 | 0.017 | 0.051 | | 0.023 | 0.068 | |
| 74675.400 | 0.025 | 0.056 | | 0.033 | 0.075 | |
| 76998.100 | 0.015 | 0.059 | | 0.019 | 0.078 | |
| 79393.000 | 0.019 | 0.055 | | 0.025 | 0.074 | |
| 81862.400 | 0.013 | 0.058 | | 0.018 | 0.077 | |

APPENDIX TABLE 10-continued

Distribution of the side chain profile of the total starch from the asBEI-asSSIII, asBEI-asSSIII-asGBSSI lines and from the corresponding wild type starch, without division into groups according to various degrees of polymerisation.

| | W (log M) | | | % of the Total Area | | |
|---|---|---|---|---|---|---|
| Molar Mass (D) | WT | asBEIasSSIII | asBEIasSSIII asGBSSI | WT | asBEIasSSIII | asBEIasSSIII asGBSSI |
| 84408.600 | 0.017 | 0.062 | | 0.023 | 0.082 | |
| 87033.900 | 0.022 | 0.072 | | 0.029 | 0.096 | |
| 89741.000 | 0.022 | 0.066 | | 0.030 | 0.088 | |
| 92532.200 | 0.029 | 0.060 | | 0.038 | 0.080 | |
| 95410.300 | 0.016 | 0.077 | | 0.021 | 0.103 | |
| 98377.800 | 0.024 | 0.072 | | 0.031 | 0.096 | |
| 101438.000 | 0.020 | 0.079 | | 0.027 | 0.104 | |
| 104593.000 | 0.021 | 0.080 | | 0.028 | 0.107 | |
| 107846.000 | 0.019 | 0.079 | | 0.025 | 0.105 | |
| 111200.000 | 0.020 | 0.086 | | 0.026 | 0.114 | |
| 114659.000 | 0.027 | 0.079 | | 0.036 | 0.105 | |
| 118225.000 | 0.032 | 0.088 | | 0.043 | 0.117 | |
| 121902.000 | 0.032 | 0.092 | | 0.043 | 0.122 | |
| 125694.000 | 0.036 | 0.095 | | 0.047 | 0.126 | |
| 129604.000 | 0.031 | 0.096 | | 0.041 | 0.127 | |
| 133635.000 | 0.037 | 0.091 | | 0.049 | 0.121 | |
| 137791.000 | 0.038 | 0.101 | | 0.050 | 0.135 | |
| 142077.000 | 0.048 | 0.100 | | 0.064 | 0.133 | |
| 146496.000 | 0.042 | 0.109 | | 0.055 | 0.144 | |
| 151052.000 | 0.040 | 0.103 | | 0.053 | 0.137 | |
| 155751.000 | 0.047 | 0.103 | | 0.062 | 0.137 | |
| 160595.000 | 0.048 | 0.113 | | 0.064 | 0.151 | |
| 165590.000 | 0.059 | 0.119 | | 0.079 | 0.158 | |
| 170740.000 | 0.056 | 0.121 | | 0.074 | 0.161 | |
| 176051.000 | 0.056 | 0.123 | | 0.074 | 0.163 | |
| 181527.000 | 0.053 | 0.121 | | 0.070 | 0.161 | |
| 187173.000 | 0.054 | 0.129 | | 0.072 | 0.172 | |
| 192995.000 | 0.066 | 0.125 | | 0.088 | 0.166 | |
| 198997.000 | 0.059 | 0.137 | | 0.078 | 0.182 | |
| 205187.000 | 0.071 | 0.128 | | 0.094 | 0.170 | |
| 211569.000 | 0.071 | 0.130 | | 0.094 | 0.173 | |
| 218149.000 | 0.074 | 0.130 | | 0.098 | 0.174 | |
| 224934.000 | 0.083 | 0.126 | | 0.110 | 0.168 | |
| 231931.000 | 0.085 | 0.133 | | 0.113 | 0.178 | |
| 239144.000 | 0.092 | 0.138 | | 0.122 | 0.183 | |
| 246583.000 | 0.087 | 0.144 | | 0.115 | 0.192 | |
| 254252.000 | 0.092 | 0.136 | | 0.123 | 0.181 | |
| 262160.000 | 0.096 | 0.138 | | 0.128 | 0.184 | |
| 270314.000 | 0.097 | 0.148 | | 0.129 | 0.197 | |
| 278722.000 | 0.105 | 0.146 | | 0.140 | 0.194 | |
| 287391.000 | 0.115 | 0.163 | | 0.153 | 0.217 | |
| 296330.000 | 0.117 | 0.157 | | 0.156 | 0.209 | |
| 305547.000 | 0.112 | 0.161 | | 0.149 | 0.215 | |
| 315050.000 | 0.126 | 0.159 | | 0.167 | 0.212 | |
| 324849.000 | 0.127 | 0.171 | | 0.168 | 0.227 | |
| 334953.000 | 0.131 | 0.179 | | 0.174 | 0.238 | |
| 345371.000 | 0.142 | 0.177 | | 0.188 | 0.236 | |
| 356113.000 | 0.137 | 0.183 | | 0.183 | 0.244 | |
| 367190.000 | 0.138 | 0.186 | | 0.183 | 0.247 | |
| 378610.000 | 0.144 | 0.198 | | 0.192 | 0.264 | |
| 390386.000 | 0.152 | 0.195 | | 0.202 | 0.259 | |
| 402529.000 | 0.163 | 0.205 | | 0.216 | 0.272 | |
| 415049.000 | 0.161 | 0.202 | | 0.214 | 0.268 | |
| 427958.000 | 0.168 | 0.206 | | 0.224 | 0.274 | |
| 441269.000 | 0.177 | 0.200 | | 0.235 | 0.266 | |
| 454994.000 | 0.182 | 0.198 | | 0.243 | 0.264 | |
| 469146.000 | 0.190 | 0.214 | | 0.252 | 0.284 | |
| 483738.000 | 0.209 | 0.213 | | 0.278 | 0.284 | |
| 498783.000 | 0.211 | 0.213 | | 0.280 | 0.283 | |
| 514297.000 | 0.222 | 0.200 | | 0.296 | 0.267 | |
| 530294.000 | 0.225 | 0.212 | | 0.300 | 0.282 | |
| 546787.000 | 0.230 | 0.203 | | 0.306 | 0.271 | |
| 563794.000 | 0.239 | 0.212 | | 0.318 | 0.282 | |
| 581330.000 | 0.251 | 0.212 | | 0.334 | 0.282 | |
| 599411.000 | 0.255 | 0.212 | | 0.339 | 0.282 | |
| 618055.000 | 0.256 | 0.220 | | 0.341 | 0.293 | |
| 637279.000 | 0.266 | 0.218 | | 0.354 | 0.291 | |
| 657100.000 | 0.273 | 0.225 | | 0.364 | 0.299 | |
| 677538.000 | 0.277 | 0.220 | | 0.368 | 0.293 | |
| 698612.000 | 0.269 | 0.226 | | 0.358 | 0.301 | |

APPENDIX TABLE 10-continued

Distribution of the side chain profile of the total starch from the asBEI-asSSIII, asBEI-asSSIII-asGBSSI lines and from the corresponding wild type starch, without division into groups according to various degrees of polymerisation.

| | W (log M) | | | % of the Total Area | | |
|---|---|---|---|---|---|---|
| Molar Mass (D) | WT | asBEIasSSIII | asBEIasSSIII asGBSSI | WT | asBEIasSSIII | asBEIasSSIII asGBSSI |
| 720341.000 | 0.274 | 0.220 | | 0.365 | 0.293 | |
| 742746.000 | 0.276 | 0.219 | | 0.367 | 0.292 | |
| 765848.000 | 0.275 | 0.218 | | 0.366 | 0.290 | |
| 789668.000 | 0.279 | 0.214 | | 0.371 | 0.284 | |
| 814229.000 | 0.271 | 0.211 | | 0.360 | 0.280 | |
| 839554.000 | 0.266 | 0.200 | | 0.354 | 0.266 | |
| 865667.000 | 0.251 | 0.206 | | 0.334 | 0.273 | |
| 892592.000 | 0.247 | 0.183 | | 0.329 | 0.244 | |
| 920355.000 | 0.235 | 0.179 | | 0.313 | 0.239 | |
| 948981.000 | 0.233 | 0.161 | | 0.310 | 0.214 | |
| 978497.000 | 0.219 | 0.156 | | 0.291 | 0.208 | |
| 1008930.000 | 0.208 | 0.151 | | 0.277 | 0.201 | |
| 1040310.000 | 0.191 | 0.136 | | 0.254 | 0.180 | |
| 1072670.000 | 0.176 | 0.132 | | 0.234 | 0.175 | |
| 1106030.000 | 0.170 | 0.106 | | 0.226 | 0.141 | |
| 1140430.000 | 0.153 | 0.099 | | 0.203 | 0.132 | |
| 1175910.000 | 0.148 | 0.089 | | 0.197 | 0.119 | |
| 1212480.000 | 0.130 | 0.081 | | 0.173 | 0.108 | |
| 1250190.000 | 0.115 | 0.071 | | 0.153 | 0.095 | |
| 1289080.000 | 0.101 | 0.061 | | 0.135 | 0.081 | |
| 1329170.000 | 0.098 | 0.046 | | 0.130 | 0.061 | |
| 1370510.000 | 0.087 | 0.035 | | 0.116 | 0.046 | |
| 1413140.000 | 0.071 | 0.030 | | 0.094 | 0.041 | |
| 1457090.000 | 0.063 | 0.022 | | 0.084 | 0.030 | |
| 1502420.000 | 0.049 | 0.018 | | 0.065 | 0.025 | |
| 1549150.000 | 0.046 | 0.008 | | 0.061 | 0.011 | |
| 1597330.000 | 0.035 | 0.005 | | 0.047 | 0.007 | |
| 1647010.000 | 0.026 | | | 0.035 | | |
| 1698240.000 | 0.021 | | | 0.028 | | |
| 1751060.000 | 0.014 | | | 0.018 | | |
| 1805520.000 | 0.015 | | | 0.019 | | |
| 1861680.000 | 0.006 | | | 0.008 | | |

What is claimed:

1. Genetically modified plant cells comprising
   (1) a first foreign nucleic acid molecule, wherein said first foreign nucleic acid molecule reduces the expression of at least one endogenous gene encoding a GBSSI protein;
   (2) a second foreign nucleic acid molecule, wherein said second foreign nucleic acid molecule reduces the expression of at least one endogenous gene encoding a SSIII protein; and
   (3) a third foreign nucleic acid molecule, wherein said third foreign nucleic acid molecule reduces the expression of at least one endogenous gene encoding a BEI protein.

2. The plant cells of claim 1, wherein said plant cells produce altered starch in comparison to starch from corresponding wild type plant cells.

3. The plant cells according to claim 2, wherein the starch exhibits an amylose content of less than 10% by weight.

4. The plant cells according to claim 3, wherein the starch comprises glucose monomers exhibiting a phosphate content at the C6-position of 30-100 nmol per mg of starch.

5. The plant cells according to claim 4, wherein the starch exhibits a higher gelatinization temperature as compared to the gelatinization temperature of starch from corresponding wild type plant cells.

6. The plant cells according to claim 5, wherein the starch exhibits an unchanged or slightly decreased DSC peak temperature as compared to the DSC peak temperature of starch from corresponding wild type plant cells.

7. The plant cells according to claim 6, wherein the starch exhibits an altered side chain distribution as compared to the side chain distribution of starch from corresponding wild type plant cells.

8. The plant cells according to claim 7, wherein the starch exhibits a freeze/thaw stability of at least 60%.

9. The plant cells according to claim 8, wherein the starch exhibits a heat stability of at least 30%.

10. The plant cells according to claim 9, wherein the starch exhibits a decreased minimum viscosity, a decreased end viscosity, a higher viscostability, or a combination thereof as compared to the minimum viscosity, end viscosity, and viscostability of starch from corresponding wild type plant cells.

11. The plant cells according to claim 10, wherein the starch exhibits a decreased gel solidity as compared to the gel solidity of starch from corresponding wild type plant cells.

12. A plant comprising the plant cells of claim 1.

13. A plant according to claim 12, wherein said plant is a potato plant.

14. Propagation material of a plant comprising the plant cells of claim 1.

15. Harvestable plant parts comprising the plant cells of claim 1.

16. A process for the production of the plant cells of claim 1, comprising introducing
   (1) a first foreign nucleic acid molecule, wherein said first foreign nucleic acid molecule reduces the expression of at least one endogenous gene encoding a GBSSI protein;

(2) a second foreign nucleic acid molecule, wherein said second foreign nucleic acid molecule reduces the expression of at least one endogenous gene encoding a SSIII protein; and (3) a third foreign nucleic acid molecule, wherein said third foreign nucleic acid molecule reduces the expression of at least one endogenous gene encoding a BEI protein into a plant cell.

17. A process for the production of a plant comprising the plant cells of claim 1, comprising:
a) producing a plant cell of claim 1 by introducing
(1) a first foreign nucleic acid molecule, wherein said first foreign nucleic acid molecule reduces the expression of at least one endogenous gene encoding a GBSSI protein;
(2) a second foreign nucleic acid molecule, wherein said second foreign nucleic acid molecule reduces the expression of at least one endogenous gene encoding a SSIII protein; and
(3) a third foreign nucleic acid molecule, wherein said third foreign nucleic acid molecule reduces the expression of at least one endogenous gene encoding a BEI protein;
b) regenerating a plant from or with the plant cell produced in a); and
c) optionally producing additional plants from the plant regenerated in b).

18. A process for the production of a starch, comprising extracting the starch produced from plant cells of claim 1, a plant comprising said plant cells, propagation material of said plant, or harvestable plant parts of said plant.

19. Propagation material of claim 14, wherein said plant is a potato plant.

20. Harvestable plant parts of claim 15, wherein said plant is a potato plant.

21. The genetically modified plant cells of claim 1, wherein said first foreign nucleic acid molecule is
(a) a DNA molecule encoding at least one antisense RNA that reduces the expression of at least one endogenous gene encoding a GBSSI protein;
(b) a DNA molecule which, via a co-suppression effect, reduces the expression of at least one endogenous gene encoding a GBSSI protein; or
(c) a DNA molecule that simultaneously encodes at least one antisense RNA and at least one sense RNA, where said antisense RNA and said sense RNA form a double-stranded RNA molecule that reduces the expression of at least one endogenous gene encoding a GBSSI protein;
said second foreign nucleic acid molecule is
(a) a DNA molecule encoding at least one antisense RNA that reduces the expression of at least one endogenous gene encoding a SSIII protein;
(b) a DNA molecule which, via a co-suppression effect, reduces the expression of at least one endogenous gene encoding a SSIII protein; or
(c) a DNA molecule that simultaneously encodes at least one antisense RNA and at least one sense RNA, where said antisense RNA and said sense RNA form a double-stranded RNA molecule that reduces the expression of at least one endogenous gene encoding a SSIII protein;
said third foreign nucleic acid molecule is
(a) a DNA molecule encoding at least one antisense RNA that reduces the expression of at least one endogenous gene encoding a BEI protein;
(b) a DNA molecule which, via a co-suppression effect, reduces the expression of at least one endogenous gene encoding a BEI protein; or
(c) a DNA molecule that simultaneously encodes at least one antisense RNA and at least one sense RNA, where said antisense RNA and said sense RNA form a double-stranded RNA molecule that reduces the expression of at least one endogenous gene encoding a BEI protein.

22. The plant cells of claim 3, wherein the starch exhibits an amylose content of less than 5% by weight.

23. The plant cells according to claim 4, wherein the starch comprises glucose monomers exhibiting a phosphate content at the C6-position of 35-85 nmol per mg of starch.

24. The plant cells according to claim 5, wherein the starch exhibits a gelatinization temperature that is increased 0.5° C.-4° C. as compared to the gelatinization temperature of starch from corresponding wild type plant cells.

25. The plant cells according to claim 2, wherein the starch exhibits a gelatinization temperature of 66° C.-68° C.

26. The plant cells according to claim 6, wherein the starch exhibits a DSC peak temperature that is decreased by a maximum of 1.5° C. as compared to the DSC peak temperature of starch from corresponding wild type plant cells.

27. The plant cells according to claim 6, wherein the starch exhibits a DSC peak temperature of 67° C.-68.5° C.

28. The plant cells according to claim 7, wherein the starch exhibits an increase in the fraction of short side chains of amylopectin with a DP of 6 by at least 100% as compared to the fraction of short side chains of amylopectin with a DP of 6 from corresponding wild type plant cells.

29. The plant cells according to claim 7, wherein the starch exhibits an increase in the fraction of short side chains of amylopectin with a DP of 8-9 by at least 15% as compared to the fraction of short side chains of amylopectin with a DP of 8-9 from corresponding wild type plant cells.

30. The plant cells according to claim 7, wherein the starch exhibits an increase in the fraction of short side chains of amylopectin with a DP of 30-34 by 5-40% as compared to the fraction of short side chains of amylopectin with a DP of 30-34 from corresponding wild type plant cells.

31. The plant cells according to claim 8, wherein the starch exhibits a freeze/thaw stability of at least 80%.

32. The plant cells according to claim 9, wherein the starch exhibits a heat stability of at least 40%.

33. The plant cells according to claim 10, wherein the starch exhibits a minimum viscosity between 30° C.-55° C.

34. The plant cells according to claim 10, wherein the starch exhibits a end viscosity between 30° C.-65° C.

35. The plant cells of claim 11, wherein the starch exhibits a higher viscostability as compared to the viscostability of starch from corresponding wild type plant cells.

36. The plant cells according to claim 11, wherein the starch exhibits a gel solidity that is decreased by at least 70% as compared to the gel solidity of starch from corresponding wild type plant cells.

37. The plant cells according to claim 2, wherein the starch exhibits a phosphate content that is increased by at least 300% as compared to the phosphate content of starch from corresponding wild type plant cells.

38. The genetically modified plant cells of claim 21, wherein
said first foreign nucleic acid molecule is
(a) a DNA molecule encoding at least one antisense RNA that reduces the expression of at least one endogenous gene encoding a GBSSI protein, said DNA molecule comprising between 20-30 nucleotides of said at least one endogenous gene; or (b) a DNA molecule which, via a co-suppression effect, reduces the expression of at least one endogenous gene encoding a GBSSI protein, said DNA molecule comprising between 20-30 nucleotides of said at least one endogenous gene;

said second foreign nucleic acid molecule is (a) a DNA molecule encoding at least one antisense RNA that reduces the expression of at least one endogenous gene encoding a SSIII protein, said DNA molecule comprising between 20-30 nucleotides of said at least one endogenous gene; or (b) a DNA molecule which, via a co-suppression effect, reduces the expression of at least one endogenous gene encoding a SSIII protein, said DNA molecule comprising between 20-30 nucleotides of said at least one endogenous gene;

said third foreign nucleic acid molecule, wherein said third foreign nucleic acid molecule is (a) a DNA molecule encoding at least one antisense RNA that reduces the expression of at least one endogenous gene encoding a BEI protein, said DNA molecule comprising between 20-30 nucleotides of at least one said endogenous gene; or (b) a DNA molecule which, via a co-suppression effect, reduces the expression of at least one endogenous gene encoding a BEI protein, said DNA molecule comprising between 20-30 nucleotides of said at least one endogenous gene.

39. The genetically modified plant cells of claim 21, wherein said first foreign nucleic acid molecule is (a) a DNA molecule encoding at least one antisense RNA that reduces the expression of at least one endogenous gene encoding a GBSSI protein, said DNA molecule comprising at least 100 nucleotides of said at least one endogenous gene; or (b) a DNA molecule which, via a co-suppression effect, reduces the expression of at least one endogenous gene encoding a GBSSI protein, said DNA molecule comprising between at least 100 nucleotides of said at least one endogenous gene;

said second foreign nucleic acid molecule is (a) a DNA molecule encoding at least one antisense RNA that reduces the expression of at least one endogenous gene encoding a SSIII protein, said DNA molecule comprising at least 100 nucleotides of said at least one endogenous gene; or (b) a DNA molecule which, via a co-suppression effect, reduces the expression of at least one endogenous gene encoding a SSIII protein, said DNA molecule comprising at least 100 nucleotides of said at least one endogenous gene;

said third foreign nucleic acid molecule, wherein said third foreign nucleic acid molecule is (a) a DNA molecule encoding at least one antisense RNA that reduces the expression of at least one endogenous gene encoding a BEI protein, said DNA molecule comprising at least 100 nucleotides of at least one said endogenous gene; or (b) a DNA molecule which, via a co-suppression effect, reduces the expression of at least one endogenous gene encoding a BEI protein, said DNA molecule comprising at least 100 nucleotides of said at least one endogenous gene.

40. The genetically modified plant cells of claim 39, wherein said first foreign nucleic acid molecule is (a) a DNA molecule encoding at least one antisense RNA that reduces the expression of at least one endogenous gene encoding a GBSSI protein, said DNA molecule comprising at least 500 nucleotides of said at least one endogenous gene; or (b) a DNA molecule which, via a co-suppression effect, reduces the expression of at least one endogenous gene encoding a GBSSI protein, said DNA molecule comprising between at least 500 nucleotides of said at least one endogenous gene;

said second foreign nucleic acid molecule is (a) a DNA molecule encoding at least one antisense RNA that reduces the expression of at least one endogenous gene encoding a SSIII protein, said DNA molecule comprising at least 500 nucleotides of said at least one endogenous gene; or (b) a DNA molecule which, via a co-suppression effect, reduces the expression of at least one endogenous gene encoding a SSIII protein, said DNA molecule comprising at least 500 nucleotides of said at least one endogenous gene;

said third foreign nucleic acid molecule, wherein said third foreign nucleic acid molecule is (a) a DNA molecule encoding at least one antisense RNA that reduces the expression of at least one endogenous gene encoding a BEI protein, said DNA molecule comprising at least 500 nucleotides of at least one said endogenous gene; or (b) a DNA molecule which, via a co-suppression effect, reduces the expression of at least one endogenous gene encoding a BEI protein, said DNA molecule comprising at least 500 nucleotides of said at least one endogenous gene.

41. The plant cells of claim 4, wherein said plant cells are potato cells.

42. The plant cells of claim 6, wherein said plant cells are potato cells.

43. The plant cells of claim 8, wherein said plant cells are potato cells.

44. The plant cells of claim 21, wherein said plant cells are potato cells.

45. The plant cells of claim 22, wherein said plant cells are potato cells.

46. The plant cells of claim 23, wherein said plant cells are potato cells.

47. The plant cells of claim 26, wherein said plant cells are potato cells.

48. The plant cells of claim 27, wherein said plant cells are potato cells.

49. The plant cells of claim 37, wherein said plant cells are potato cells.

* * * * *